(12) United States Patent
Muramatsu et al.

(10) Patent No.: US 6,358,720 B1
(45) Date of Patent: Mar. 19, 2002

(54) SERINE/THEONINE PROTEIN KINASE

(75) Inventors: Masaaki Muramatsu; Takuji Shirasawa, both of Tokyo; Hiroshi Tokumitsu, Kagawa; Teruhisa Noguchi, Tokyo, all of (JP)

(73) Assignee: Helix Research Institute, Chiba (JP)

( * ) Notice: Subject to any disclaimer, the term of this patent is extended or adjusted under 35 U.S.C. 154(b) by 0 days.

(21) Appl. No.: 09/428,711

(22) Filed: Oct. 28, 1999

Related U.S. Application Data

(63) Continuation-in-part of application No. PCT/JP98/01246, filed on Mar. 23, 1998.

(30) Foreign Application Priority Data

Apr. 28, 1997 (JP) .............................................. 9-124798

(51) Int. Cl.$^7$ ................................................. C12N 9/12
(52) U.S. Cl. .................. 435/194; 435/183; 435/252.33; 435/320.1; 536/23.2
(58) Field of Search ......................... 435/252.33, 320.1, 435/183, 194; 536/23.2

(56) References Cited

U.S. PATENT DOCUMENTS 5,643,758 A * 7/1997 Guan et al. ................. 435/69.7

OTHER PUBLICATIONS

Ogura et al. Accession Z38016, Mar. 1995.*
Asah. Accession Q87512, Nov. 22, 1995.*
Beach et al. Accession Q63490, Dec. 7, 1994.*
Meyerson. Accession X66362, May 3, 1993.*
Li et al. Accession U58198, Jun. 24, 1996.*
Marra et al. Accession W57008, Jun. 4, 1996.*

* cited by examiner

*Primary Examiner*—Ponnathapu Achutamurthy
*Assistant Examiner*—Christian L. Fronda
(74) *Attorney, Agent, or Firm*—Fish & Richardson P.C.

(57) ABSTRACT

A mouse CDNA encoding a protein comprising a serine/threonine protein kinase region was isolated by effecting PCR using a synthetic DNA corresponding to the kinase-conserved region as a primer and a rat cDNA as a template. A mouse cDNA library was screened using the DNA fragment thus obtained as a probe. The multiple human and mouse cDNAs having the similar structure to the isolated mouse cDNA were successfully isolated based on the sequence of the isolated mouse cDNA. An antisense DNA against the isolated mouse cDNA was synthesized, and its effect on a nerve cell was studied to confirm that the antisense DNA inhibits axonal elongation.

18 Claims, 4 Drawing Sheets

1. COS7
2. COS7/pME-MUK1

| | | | | | | |
|---|---|---|---|---|---|---|
| MJK1-prot | 1 | MEPGRGGVET | VGKFEFSRKD | LIGHGAFAVV | FKGRHREKHD | LEVAVKCINK | 50 |
| MJK2-prot | 1 | MEVVGD---- | ---FEYCKRD | LVGHGAFAVV | FRGRHRQKTD | WEVAIKSINK | 50 |
| unc-51-prot | 1 | MEQFDG---- | ---FEYSKRD | LLGHGAFAIV | YRGRYVDRTD | VPVAIKAIAK | 50 |
| | | | | | | | |
| MJK1-prot | 51 | KNLAKSQTLL | GKEIKILKEL | K---HENIVA | LYDFQEMANS | VYLVMEYCNG | 100 |
| MJK2-prot | 51 | KNLSKSQILL | GKEIKILKEL | Q---HENIVA | LYDVQELPNS | VFLVMEYCNG | 100 |
| unc-51-prot | 51 | KNISKSKNLL | TKEIKILKEL | SSLKHENLVG | LLKCTETPTH | VYLVMEFCNG | 100 |
| | | | | | | | |
| MJK1-prot | 101 | GDLADYLHTM | RTLSEDTVRL | FLQQIAGAMR | LLHSKGIIHR | DLKPQNILLS | 150 |
| MJK2-prot | 101 | GDLADYLQAK | GTLSEDTIRV | FLHQIAAAMR | ILHSKGIIHR | DLKPQNILLS | 150 |
| unc-51-prot | 101 | GDLADYLQQK | TTLNEDTIQH | FVVQIAHALE | AINKKGIVHR | DLKPQNILLC | 150 |
| | | | | | | | |
| MJK1-prot | 151 | NPGGRRANPS | N-IRVKIADF | GFARYLQSNM | MAATLCGSPM | YMAPEVIMSQ | 200 |
| MJK2-prot | 151 | YANRRKSNVS | G-IRIKIADF | GFARYLHSNT | MAATLCGSPM | YMAPEVIMSQ | 200 |
| unc-51-prot | 151 | NNSRTQNPHF | TDIVIKLADF | GFARFLNDGV | MAATLCGSPM | YMAPEVIMSM | 200 |
| | | | | | | | |
| MJK1-prot | 201 | HYDGKADLWS | IGTIVYQCLT | GKAPFQASSP | QDLRLFYEKN | KTLVPAIPRE | 250 |
| MJK2-prot | 201 | HYDAKADLWS | IGTVIYQCLV | GKPPFQANSP | QDLRMFYEKN | RSLMPSIPRE | 250 |
| unc-51-prot | 201 | QYDAKADLWS | IGTILFQCLT | GKAPFVAQTP | PQLKAYYEKT | RELRPNIPEW | 250 |
| | | | | | | | |
| MJK1-prot | 251 | TSAPLRQLLL | ALLQRNHKDR | MDFDEFFHHP | FLDASTPIKK | SPPVPVPSYP | 300 |
| MJK2-prot | 251 | TSPYLANLLL | GLLQRNQKDR | MDFEAFFSHP | FLEQ-VPVKK | SCPVPVPVYS | 300 |
| unc-51-prot | 251 | CSPNLRDLLL | RLLKRNAKDR | ISFEDFFNHP | FLTS--PLLP | SPSKRILESA | 300 |
| | | | | | | | |
| MJK1-prot | 301 | SSGSGSSSSS | SSASHLASPP | SLGEM--PQL | QKTLTSPADA | AGFLQGSRDS | 350 |
| MJK2-prot | 301 | GPVPGSSCSS | SPSCRFASPP | SLPDMQHIQE | ENLSSPPLGP | PNYLQVSKDS | 350 |
| unc-51-prot | 301 | RSPLLANRRI | ITPQSSLPVP | KRAGSTKLDS | PTPVRRIGES | PRVQRRVITP | 350 |
| | | | | | | | |
| MJK1-prot | 351 | -GGSSKDS-C | DTDDFVMVPA | QFPGDLVAEA | ASAKPPPDSL | LCSGSSLVAS | 400 |
| MJK2-prot | 351 | ASNSSKNSSC | DTDDFVLV-- | ---------- | ---------- | -----HNIS | 400 |
| unc-51-prot | 351 | GMPSPVPGAP | MQESTDFT-- | ---------- | ---------- | ---------- | 400 |
| | | | | | | | |
| MJK1-prot | 401 | AGLESHGRTP | SPSPTCSSSP | SPSGRPGPFS | SNRYGASVPI | PVPTQVHNYQ | 450 |
| MJK2-prot | 401 | SDHSYDMPMG | TTARRASNEF | FMCGGQCQPT | VSPHSETAPI | PVPTQVRNYQ | 450 |
| unc-51-prot | 401 | ---------- | FLPPRQESSP | VKQVQVHTNV | SPSLTTCKPV | PVPSQRLTYQ | 450 |
| | | | | | | | |
| MJK1-prot | 451 | RIEQNLQSPT | QQQTA----- | -RSSAIRRSG | STSPLGFGRA | -SPSPPSHTD | 500 |
| MJK2-prot | 451 | RIEQNLISTA | SSGTNPHGSP | -RSAVVRRS- | NTSPMGFLRV | GSCSPVPGDT | 500 |
| unc-51-prot | 451 | KMEERLAAAR | KTAVPSSSSP | TGSAVSAQHQ | HQHQQQQEPA | SSPVVQRIER | 500 |
| | | | | | | | |
| MJK1-prot | 501 | GAMLARKLSL | GGGRPYTPSP | QVGTIPERPS | WSRVPSPQGA | DVRVGRSPRP | 550 |
| MJK2-prot | 501 | VQTGGRRLST | GSSRPYSPSP | LVGTIPEQFS | QCCCGHPQGH | EARSRHSSGS | 550 |
| unc-51-prot | 501 | PDQLPRRTTL | QDPNAHDIER | MTMPNPTFVV | CGSSTKPSPN | NANRVRRSTI | 550 |

FIG. 3

```
MUK1-prot    551 GSSVPEHSPR TTGLGCRLHS APNLSDFHVV RPKLPKPPTD PRTNKNG...     600
MUK2-prot    551 PVP-QTQAPQ SLLLGARLQS APTLIDIYQN KQKLRKQHSD PVCPSHAGAG     600
unc-51-prot  551 TSPADTQ--D MVAADQMLSN LDPTTTTTTI PKSATTANIQ GIPRGARDRS     600

MUK1-prot    601 .......... .......... .......... .......... ..........     650
MUK2-prot    601 YSYSPQPSRP GSLGTSPTKH TGSSPRNSDW FFKTPLPTII GSPTKTTAPF     650
unc-51-prot  601 VTSPPQPTIH ENEPLDNAKY QQTDVNNSPT APTEPFIIKN QTTCSTSSTS     650

MUK1-prot    651 .......... .......... .......... .......... ..........     700
MUK2-prot    651 KIPKTQASSN LLALVTRHGP AESQSKDGND PRECSHCLSV QGSERHRSEQ     700
unc-51-prot  651 ---------- ---------- ---------- ---------- ----------     700

MUK1-prot    701 .......... .......... .......... .......... ..........     750
MUK2-prot    701 QQSKAVFGRS VSTGKLSEQQ VKAPLGGHQG STDSLNTERP MDVAPAGACG     750
unc-51-prot  701 ---------- ---------- ---------- ---------- ----------     750

MUK1-prot    751 .......... .......... .......... .......... ..........     800
MUK2-prot    751 VMLALPAGTA ASARAVLFTV GSPPHSATAP TCTHMVLRTR TTSVGSSSSG     800
unc-51-prot  751 ---------- ---------- ---------- ---------- ----------     800

MUK1-prot    801 .......... .......... .......... .......... ..........     850
MUK2-prot    801 GSLCSASGRV CVGSPPGPGL GSSPPGAEGA PSLRYVPYGA SPPSLEGLIT     850
unc-51-prot  801 ---------- --------SS VVEEEEAMSL PFASGSHLAA GFKKTPAEVP     850

MUK1-prot    851 .......... .......... .......... .......... ..........     900
MUK2-prot    851 FEAPELPEET LMEREHTDTL RHLNMMLMFT ECVLDLTAVR GGNPELCTSA     900
unc-51-prot  851 MDHGALPPAL DQEIVLGEEH KQILAKLRFV AELVDTLIHV AEQKDNPLAS     900

MUK1-prot    901 .......... .......... .......... .......... ..........     950
MUK2-prot    901 VSLYQIQESV VVDQISQLSK DWGRVEQLVL YMKAAQLLAA SLHLAKAQVK     950
unc-51-prot  901 AMASRRQLLT TGTSTTNTSS PYRRAEQLVV YVRALHMLSS ALLLAQTNVA     950

MUK1-prot    951 .......... .......... .......... .......... ..........    1000
MUK2-prot    951 SGKLSPSMAV KQVVKNLNER YKFCITMCKK LTEKLNRFFS DKQRFIDEIN    1000
unc-51-prot  951 NRVLHPSVAV QQVLNQLNDK YHQCLVRSQE L------ASL GLPGQDPAMA    1000

MUK1-prot   1001 .......... .......... .......... .......... ..........    1050
MUK2-prot   1001 SVTAEKLIYN CAVEMVQSAA LDEMFQQTED IVYRYHKAAV LLEGLSKILQ    1050
unc-51-prot 1001 VISAERIMYR HAIELCQAAA LDELFGNPQL CSQRYQTAYM MLHTLAEQVN    1050

MUK1-prot   1051 .......... .......... .......... .......... ..........    1100
MUK2-prot   1051 DPTDVENVHK YKCSIERRLS ALCCSTATV. .......... ..........    1100
unc-51-prot 1051 CDQDKTVLTR YKVAVEKRLR ILERQGFVAA VNT....... ..........    1100
```

FIG. 4

SEQUENCE LISTING

```
<160> NUMBER OF SEQ ID NOS:  21

<210> SEQ ID NO 1
<211> LENGTH: 2673
<212> TYPE: DNA
<213> ORGANISM: Mus musculus
<220> FEATURE:
<221> NAME/KEY: CDS
<222> LOCATION: (1)...(1746)

<400> SEQUENCE: 1 atg gag ccg ggc cgc ggc ggc gtc gag acc gtg ggc aag ttc gag ttc      48
Met Glu Pro Gly Arg Gly Gly Val Glu Thr Val Gly Lys Phe Glu Phe
  1               5                  10                  15 tct cgc aag gac ctg att gga cac ggc gcc ttc gcg gtg gtc ttc aag      96
Ser Arg Lys Asp Leu Ile Gly His Gly Ala Phe Ala Val Val Phe Lys
               20                  25                  30 ggt cga cac cgc gag aag cac gac ctg gag gtg gcc gtc aaa tgc att     144
Gly Arg His Arg Glu Lys His Asp Leu Glu Val Ala Val Lys Cys Ile
           35                  40                  45 aac aag aag aac ctt gcc aag tcc caa aca ctg ctg gga aag gaa atc     192
Asn Lys Lys Asn Leu Ala Lys Ser Gln Thr Leu Leu Gly Lys Glu Ile
       50                  55                  60 aaa atc ctg aag gaa cta aag cac gaa aac atc gtg gcg ctg tat gac     240
Lys Ile Leu Lys Glu Leu Lys His Glu Asn Ile Val Ala Leu Tyr Asp
   65                  70                  75                  80 ttc cag gaa atg gct aat tct gtc tac ctg gtc atg gag tat tgt aat     288
Phe Gln Glu Met Ala Asn Ser Val Tyr Leu Val Met Glu Tyr Cys Asn
                   85                  90                  95 ggt gga gac ctg gct gac tac ctg cac act atg cgc aca ctg agt gaa     336
Gly Gly Asp Leu Ala Asp Tyr Leu His Thr Met Arg Thr Leu Ser Glu
              100                 105                 110 gac act gtc agg ctt ttc cta cag cag atc gct ggc gcc atg cgg ctg     384
Asp Thr Val Arg Leu Phe Leu Gln Gln Ile Ala Gly Ala Met Arg Leu
          115                 120                 125
```

-continued

| | |
|---|---|
| ctg cac agc aag ggc atc atc cac cgg gac ctg aag ccc cag aac atc<br>Leu His Ser Lys Gly Ile Ile His Arg Asp Leu Lys Pro Gln Asn Ile<br>130                        135                   140 | 432 |
| ctg ctg tcc aac cct ggg ggc cgc cgg gcc aac ccc agc aac atc cga<br>Leu Leu Ser Asn Pro Gly Gly Arg Arg Ala Asn Pro Ser Asn Ile Arg<br>145                    150                     155                160 | 480 |
| gtc aag att gct gac ttt gga ttc gct cgg tac ctc cag agc aac atg<br>Val Lys Ile Ala Asp Phe Gly Phe Ala Arg Tyr Leu Gln Ser Asn Met<br>                 165                   170                  175 | 528 |
| atg gcg gcc aca ctc tgt ggt tct cct atg tac atg gct cct gag gtc<br>Met Ala Ala Thr Leu Cys Gly Ser Pro Met Tyr Met Ala Pro Glu Val<br>180                        185                   190 | 576 |
| att atg tcc cag cac tac gat gga aag gct gac ctg tgg agc att ggc<br>Ile Met Ser Gln His Tyr Asp Gly Lys Ala Asp Leu Trp Ser Ile Gly<br>                 195                   200                  205 | 624 |
| acc att gtc tac cag tgt ctg aca ggg aag gcc cct ttt cag gcc agc<br>Thr Ile Val Tyr Gln Cys Leu Thr Gly Lys Ala Pro Phe Gln Ala Ser<br>210                        215                   220 | 672 |
| agc cct cag gat ttg cgc ctg ttt tat gag aag aac aag aca cta gtt<br>Ser Pro Gln Asp Leu Arg Leu Phe Tyr Glu Lys Asn Lys Thr Leu Val<br>225                        230                   235               240 | 720 |
| cct gcc atc ccc cgg gag aca tca gct ccc ctg cgg cag ctc ctc ctg<br>Pro Ala Ile Pro Arg Glu Thr Ser Ala Pro Leu Arg Gln Leu Leu Leu<br>                    245                   250                  255 | 768 |
| gct ctg ttg cag cgg aac cac aag gac cgc atg gac ttt gat gaa ttt<br>Ala Leu Leu Gln Arg Asn His Lys Asp Arg Met Asp Phe Asp Glu Phe<br>260                        265                   270 | 816 |
| ttc cac cac cct ttc ttg gat gcc agc acc ccc atc aag aaa tcc cca<br>Phe His His Pro Phe Leu Asp Ala Ser Thr Pro Ile Lys Lys Ser Pro<br>                 275                   280                  285 | 864 |
| cct gtg cct gtg ccc tca tat cca agc tca ggg tct ggc agc agc tcc<br>Pro Val Pro Val Pro Ser Tyr Pro Ser Ser Gly Ser Gly Ser Ser Ser<br>290                        295                   300 | 912 |
| agc agc agc tct gcc tcc cac ctg gcc tct cca ccg tcc ctg ggg gag<br>Ser Ser Ser Ser Ala Ser His Leu Ala Ser Pro Pro Ser Leu Gly Glu<br>305                        310                   315               320 | 960 |
| atg cca cag cta cag aag acc ctt acc tcc cca gcc gat gct gct ggc<br>Met Pro Gln Leu Gln Lys Thr Leu Thr Ser Pro Ala Asp Ala Ala Gly<br>                    325                   330                  335 | 1008 |
| ttt ctt cag ggc tcc cgg gac tct ggt ggc agc agc aaa gac tcc tgt<br>Phe Leu Gln Gly Ser Arg Asp Ser Gly Gly Ser Ser Lys Asp Ser Cys<br>                 340                   345                  350 | 1056 |
| gac aca gat gac ttt gtc atg gtc cca gcc cag ttt cca ggt gat cta<br>Asp Thr Asp Asp Phe Val Met Val Pro Ala Gln Phe Pro Gly Asp Leu<br>                 355                   360                  365 | 1104 |
| gtt gct gag gca gcc agt gcc aag ccc cca cct gat agc ctg ctg tgt<br>Val Ala Glu Ala Ala Ser Ala Lys Pro Pro Pro Asp Ser Leu Leu Cys<br>370                        375                   380 | 1152 |
| agt ggg agc tca ttg gtg gcc tct gct ggc cta gag agc cac ggc cgt<br>Ser Gly Ser Ser Leu Val Ala Ser Ala Gly Leu Glu Ser His Gly Arg<br>385                        390                   395               400 | 1200 |
| acc ccc tct ccc tct ccg acc tgc agc agc tct ccc agc ccc tct ggc<br>Thr Pro Ser Pro Ser Pro Thr Cys Ser Ser Ser Pro Ser Pro Ser Gly<br>                 405                   410                  415 | 1248 |
| cgg cct ggc ccc ttc tcc agc aac agg tac ggt gcc tcg gtc ccc att<br>Arg Pro Gly Pro Phe Ser Ser Asn Arg Tyr Gly Ala Ser Val Pro Ile<br>                    420                   425                  430 | 1296 |
| cct gtc ccc act cag gtg cac aat tac cag cgc atc gag caa aac ctg<br>Pro Val Pro Thr Gln Val His Asn Tyr Gln Arg Ile Glu Gln Asn Leu<br>                 435                   440                  445 | 1344 |

-continued

```
caa tcg ccc act caa cag cag aca gcc cgg tcc tct gcc atc cga agg    1392
Gln Ser Pro Thr Gln Gln Gln Thr Ala Arg Ser Ser Ala Ile Arg Arg
        450                 455                 460 tca ggg agc acc agc ccc ctg ggc ttt ggc cgg gcc agc cca tca ccc    1440
Ser Gly Ser Thr Ser Pro Leu Gly Phe Gly Arg Ala Ser Pro Ser Pro
465                 470                 475                 480 ccc tcc cac acc gat ggg gcc atg ctg gcc agg aag ctg tca ctt gga    1488
Pro Ser His Thr Asp Gly Ala Met Leu Ala Arg Lys Leu Ser Leu Gly
                485                 490                 495 ggt ggc cgt ccc tac aca cct tct ccc caa gtg gga acc atc cca gag    1536
Gly Gly Arg Pro Tyr Thr Pro Ser Pro Gln Val Gly Thr Ile Pro Glu
            500                 505                 510 cga ccc agc tgg agc aga gtg ccc tcc cca caa gga gct gat gtg cgg    1584
Arg Pro Ser Trp Ser Arg Val Pro Ser Pro Gln Gly Ala Asp Val Arg
        515                 520                 525 gtt ggc agg tca cca cga ccc ggt tcc tct gtg cct gag cac tct cca    1632
Val Gly Arg Ser Pro Arg Pro Gly Ser Ser Val Pro Glu His Ser Pro
530                 535                 540 aga acc act ggg ctg ggc tgc cgc ctg cac agt gcc cct aac ctg tcc    1680
Arg Thr Thr Gly Leu Gly Cys Arg Leu His Ser Ala Pro Asn Leu Ser
545                 550                 555                 560 gac ttc cat gtt gtg cgt ccc aag ctg cct aag ccc cca aca gac ccc    1728
Asp Phe His Val Val Arg Pro Lys Leu Pro Lys Pro Pro Thr Asp Pro
                565                 570                 575 cgt act aac aaa aat ggc taataacgaa atggctaatg catggtcaat          1776
Arg Thr Asn Lys Asn Gly
                580 ccccggcccc cgttttttcg cattccaagc cgcattgaag ataatgaagc ctatcatcgc    1836
cagcgttagc cacaaattgt tgactcggaa atatacttt agcaagtaac ccacgataaa    1896
tagttgtaca acagcccgca cgacaccaat gacgatgtcc ctatctaagc caagtttctg    1956
ccacaaacta attcctaacg cgacgagcac taacattgcc gccaaaaata gtgacgtatt    2016
attaactgct aaattcatgc gtgtacctcc aatctgccag caaccacttt cgctaactga    2076
tctgccgcag caatctctgt cgcgtcatga gtaatcatga tcgttgtcac gtgatcctgc    2136
tcatttaact gtcgtaacca ggcgtgcacg atttgcttat tattttcatc caaaccagct    2196
gtcacctcat ctaataacaa cacttttggt aagaataaga tgttgcgaag cagcgcgacc    2256
cgctgccgtt caccaccgga aagctcgata atcggctgat gcagggttcg ttcggacagc    2316
ccaacattat ttaacgccgt taccactcgt tgcgtatcca tgcttgcttt acgaatttgg    2376
tacgggaaag ctaagttatc tgctaccgtc tcaccaaata acgtcggttg ttggaaacaa    2436
tatgagactt gccgccgata catgattggg tcataacttt caatcggctg cccatcaaaa    2496
atcaaggtcc cacttgtttt agaaatcatg gccgcaatga tccgtaataa cgtactttc    2556
ccaccaccgg atggtcccgt caatgtaata tgagccccag ctggaatctg ccaatcaaca    2616
tcatgtaaaa tatgttgatc agcgatttga taattaactt tttctaaact aatcaat       2673
```

<210> SEQ ID NO 2
<211> LENGTH: 582
<212> TYPE: PRT
<213> ORGANISM: Mus musculus

<400> SEQUENCE: 2

```
Met Glu Pro Gly Arg Gly Gly Val Glu Thr Val Gly Lys Phe Glu Phe
  1               5                  10                  15

Ser Arg Lys Asp Leu Ile Gly His Gly Ala Phe Ala Val Val Phe Lys
```

-continued

```
                 20                  25                  30
Gly Arg His Arg Glu Lys His Asp Leu Glu Val Ala Val Lys Cys Ile
             35                  40                  45
Asn Lys Lys Asn Leu Ala Lys Ser Gln Thr Leu Leu Gly Lys Glu Ile
 50                  55                  60
Lys Ile Leu Lys Glu Leu Lys His Glu Asn Ile Val Ala Leu Tyr Asp
 65                  70                  75                  80
Phe Gln Glu Met Ala Asn Ser Val Tyr Leu Val Met Glu Tyr Cys Asn
                 85                  90                  95
Gly Gly Asp Leu Ala Asp Tyr Leu His Thr Met Arg Thr Leu Ser Glu
                100                 105                 110
Asp Thr Val Arg Leu Phe Leu Gln Gln Ile Ala Gly Ala Met Arg Leu
                115                 120                 125
Leu His Ser Lys Gly Ile Ile His Arg Asp Leu Lys Pro Gln Asn Ile
            130                 135                 140
Leu Leu Ser Asn Pro Gly Gly Arg Arg Ala Asn Pro Ser Asn Ile Arg
145                 150                 155                 160
Val Lys Ile Ala Asp Phe Gly Phe Ala Arg Tyr Leu Gln Ser Asn Met
                165                 170                 175
Met Ala Ala Thr Leu Cys Gly Ser Pro Met Tyr Met Ala Pro Glu Val
                180                 185                 190
Ile Met Ser Gln His Tyr Asp Gly Lys Ala Asp Leu Trp Ser Ile Gly
                195                 200                 205
Thr Ile Val Tyr Gln Cys Leu Thr Gly Lys Ala Pro Phe Gln Ala Ser
            210                 215                 220
Ser Pro Gln Asp Leu Arg Leu Phe Tyr Glu Lys Asn Lys Thr Leu Val
225                 230                 235                 240
Pro Ala Ile Pro Arg Glu Thr Ser Ala Pro Leu Arg Gln Leu Leu Leu
                245                 250                 255
Ala Leu Leu Gln Arg Asn His Lys Asp Arg Met Asp Phe Asp Glu Phe
                260                 265                 270
Phe His His Pro Phe Leu Asp Ala Ser Thr Pro Ile Lys Lys Ser Pro
            275                 280                 285
Pro Val Pro Val Pro Ser Tyr Pro Ser Ser Gly Ser Gly Ser Ser Ser
            290                 295                 300
Ser Ser Ser Ser Ala Ser His Leu Ala Ser Pro Pro Ser Leu Gly Glu
305                 310                 315                 320
Met Pro Gln Leu Gln Lys Thr Leu Thr Ser Pro Ala Asp Ala Ala Gly
                325                 330                 335
Phe Leu Gln Gly Ser Arg Asp Ser Gly Gly Ser Ser Lys Asp Ser Cys
            340                 345                 350
Asp Thr Asp Asp Phe Val Met Val Pro Ala Gln Phe Pro Gly Asp Leu
            355                 360                 365
Val Ala Glu Ala Ala Ser Ala Lys Pro Pro Asp Ser Leu Leu Cys
            370                 375                 380
Ser Gly Ser Ser Leu Val Ala Ser Ala Gly Leu Glu Ser His Gly Arg
385                 390                 395                 400
Thr Pro Ser Pro Ser Pro Thr Cys Ser Ser Pro Ser Pro Ser Gly
                405                 410                 415
Arg Pro Gly Pro Phe Ser Ser Asn Arg Tyr Gly Ala Ser Val Pro Ile
            420                 425                 430
Pro Val Pro Thr Gln Val His Asn Tyr Gln Arg Ile Glu Gln Asn Leu
            435                 440                 445
```

```
Gln Ser Pro Thr Gln Gln Thr Ala Arg Ser Ser Ala Ile Arg Arg
    450             455                 460

Ser Gly Ser Thr Ser Pro Leu Gly Phe Gly Arg Ala Ser Pro Ser Pro
465             470                 475                 480

Pro Ser His Thr Asp Gly Ala Met Leu Ala Arg Lys Leu Ser Leu Gly
            485                 490                 495

Gly Gly Arg Pro Tyr Thr Pro Ser Pro Gln Val Gly Thr Ile Pro Glu
            500                 505                 510

Arg Pro Ser Trp Ser Arg Val Pro Ser Pro Gln Gly Ala Asp Val Arg
            515                 520                 525

Val Gly Arg Ser Pro Arg Pro Gly Ser Ser Val Pro Glu His Ser Pro
    530             535                 540

Arg Thr Thr Gly Leu Gly Cys Arg Leu His Ser Ala Pro Asn Leu Ser
545             550                 555                 560

Asp Phe His Val Val Arg Pro Lys Leu Pro Lys Pro Pro Thr Asp Pro
                565                 570                 575

Arg Thr Asn Lys Asn Gly
            580
```

<210> SEQ ID NO 3
<211> LENGTH: 423
<212> TYPE: DNA
<213> ORGANISM: Homo sapiens
<220> FEATURE:
<221> NAME/KEY: CDS
<222> LOCATION: (1)...(423)

<400> SEQUENCE: 3

```
gac aac atc ctg ctg tcc aac ccc gcc ggc cgc cgc gcc aac ccc aac      48
Asp Asn Ile Leu Leu Ser Asn Pro Ala Gly Arg Arg Ala Asn Pro Asn
  1               5                  10                  15 agc atc cgc gtc aag atc gct gac ttc ggc ttc cgg cgg tac ctc cag      96
Ser Ile Arg Val Lys Ile Ala Asp Phe Gly Phe Arg Arg Tyr Leu Gln
             20                  25                  30 agc aac atg atg gcg gcc aca ctc tgc ggc tcc ccc atg tac atg gcc     144
Ser Asn Met Met Ala Ala Thr Leu Cys Gly Ser Pro Met Tyr Met Ala
         35                  40                  45 ccc gag gtc atc atg tcc cag cac tac gac ggg aag gcg gac ctg tgg     192
Pro Glu Val Ile Met Ser Gln His Tyr Asp Gly Lys Ala Asp Leu Trp
     50                  55                  60 agc atc ggc acc atc gta tac cag tgc ctg acg ggg aag gcg ccc ttt     240
Ser Ile Gly Thr Ile Val Tyr Gln Cys Leu Thr Gly Lys Ala Pro Phe
 65                  70                  75                  80 cag gcc agc agc cca gac ctg cgc ctg ttt tac gag aag aac aag acg     288
Gln Ala Ser Ser Pro Asp Leu Arg Leu Phe Tyr Glu Lys Asn Lys Thr
                 85                  90                  95 ttg gtc ccc acc atc ccc cgg gag acc tcg gcc ccg ctg cgg cag ctg     336
Leu Val Pro Thr Ile Pro Arg Glu Thr Ser Ala Pro Leu Arg Gln Leu
            100                 105                 110 ctc ctg gcc cta ctg caa cgc aac cac aag gac cgc atg gac ttc gat     384
Leu Leu Ala Leu Leu Gln Arg Asn His Lys Asp Arg Met Asp Phe Asp
        115                 120                 125 gag ttt ttt cat cac cct ttc ctc gat gcc agc ccc tcg                 423
Glu Phe Phe His His Pro Phe Leu Asp Ala Ser Pro Ser
    130                 135                 140
```

<210> SEQ ID NO 4
<211> LENGTH: 141
<212> TYPE: PRT

```
<213> ORGANISM: Homo sapiens

<400> SEQUENCE: 4

Asp Asn Ile Leu Leu Ser Asn Pro Ala Gly Arg Arg Ala Asn Pro Asn
  1               5                  10                  15

Ser Ile Arg Val Lys Ile Ala Asp Phe Gly Phe Arg Arg Tyr Leu Gln
             20                  25                  30

Ser Asn Met Met Ala Ala Thr Leu Cys Gly Ser Pro Met Tyr Met Ala
         35                  40                  45

Pro Glu Val Ile Met Ser Gln His Tyr Asp Gly Lys Ala Asp Leu Trp
     50                  55                  60

Ser Ile Gly Thr Ile Val Tyr Gln Cys Leu Thr Gly Lys Ala Pro Phe
 65                  70                  75                  80

Gln Ala Ser Ser Pro Asp Leu Arg Leu Phe Tyr Glu Lys Asn Lys Thr
                 85                  90                  95

Leu Val Pro Thr Ile Pro Arg Glu Thr Ser Ala Pro Leu Arg Gln Leu
            100                 105                 110

Leu Leu Ala Leu Leu Gln Arg Asn His Lys Asp Arg Met Asp Phe Asp
        115                 120                 125

Glu Phe Phe His His Pro Phe Leu Asp Ala Ser Pro Ser
    130                 135                 140

<210> SEQ ID NO 5
<211> LENGTH: 7
<212> TYPE: PRT
<213> ORGANISM: Artificial Sequence
<220> FEATURE:
<223> OTHER INFORMATION: Kinase-conserved region VIb

<400> SEQUENCE: 5

Ile Ser His Arg Glu Leu Gln
 1               5

<210> SEQ ID NO 6
<211> LENGTH: 6
<212> TYPE: PRT
<213> ORGANISM: Artificial Sequence
<220> FEATURE:
<223> OTHER INFORMATION: Kinase-conserved region VIII

<400> SEQUENCE: 6

Arg Tyr Met Ala Pro Glu
 1               5

<210> SEQ ID NO 7
<211> LENGTH: 20
<212> TYPE: DNA
<213> ORGANISM: Artificial Sequence
<220> FEATURE:
<223> OTHER INFORMATION: Synthetically generated primer
<221> NAME/KEY: misc_feature
<222> LOCATION: (1)...(20)
<223> OTHER INFORMATION: n = A,T,C or G

<400> SEQUENCE: 7
athtcncayc gngayttraa                                          20

<210> SEQ ID NO 8
<211> LENGTH: 17
<212> TYPE: DNA
<213> ORGANISM: Artificial Sequence
<220> FEATURE:
<223> OTHER INFORMATION: Synthetically generated DNA
```

-continued

```
<221> NAME/KEY: misc_feature
<222> LOCATION: (1)...(17)
<223> OTHER INFORMATION: n = A,T,C or G

<400> SEQUENCE: 8
ctnggngcca trtayct                                                  17

<210> SEQ ID NO 9
<211> LENGTH: 114
<212> TYPE: DNA
<213> ORGANISM: Rattus norvegicus

<400> SEQUENCE: 9
gccatgtacc tattacatct tctaatgtgt caccctgatt atataaattt aactagacac   60
taccttccaa agtttgtatc agtgctcata tttgaattca agtcccggtg cgag         114

<210> SEQ ID NO 10
<211> LENGTH: 16
<212> TYPE: PRT
<213> ORGANISM: Artificial Sequence
<220> FEATURE:
<223> OTHER INFORMATION: Synthetically generated protein

<400> SEQUENCE: 10

Cys Ala Arg Ser Ser Ala Ile Arg Arg Ser Gly Ser Thr Ser Pro Leu
  1               5                  10                  15

<210> SEQ ID NO 11
<211> LENGTH: 21
<212> TYPE: DNA
<213> ORGANISM: Artificial Sequence
<220> FEATURE:
<223> OTHER INFORMATION: Synthetically generated DNA

<400> SEQUENCE: 11
gaacttgccc acggtctcga c                                             21

<210> SEQ ID NO 12
<211> LENGTH: 21
<212> TYPE: DNA
<213> ORGANISM: Artificial Sequence
<220> FEATURE:
<223> OTHER INFORMATION: Synthetically generated DNA

<400> SEQUENCE: 12
gtcgagaccg tgggcaagtt c                                             21

<210> SEQ ID NO 13
<211> LENGTH: 3995
<212> TYPE: DNA
<213> ORGANISM: Mus musculus
<220> FEATURE:
<221> NAME/KEY: CDS
<222> LOCATION: (388)...(3540)
<221> NAME/KEY: misc_feature
<222> LOCATION: (1)...(3995)
<223> OTHER INFORMATION: n = A,T,C or G

<400> SEQUENCE: 13
gtccgcctcn acgcagtgct gcgccggcac ctcgggctcc gaggcccggg tgccgcggat   60
cttttgtttc tgcggggctc cgagccgcat cgtcagtcag gcccggactt ggagctggag  120
tgtgtcagag ctgagtcccg agtcgaccgg tcccgactgt cagcgccgga gggtaccgag  180
nagnacgccg agggagcgcg cccctcngtc cgccggcctg tgggactggg acccggctca  240
```

```
ggcctgcccg atggggcacg gggccctggc gatgagcccg cgcctccgtc cccgtacgcg      300
gcccggccgg cctccgcctg agcccagcgc accccgtagc gccgcccctg ggcccgagcc      360
cgctcgcgcc cccggcccgc gcgcgct atg gag ccg ggc cgc ggc ggc gtc gag      414
                              Met Glu Pro Gly Arg Gly Gly Val Glu
                              1               5 acc gtg ggc aag ttc gag ttc tct cgc aag gac ctg att gga cac ggc        462
Thr Val Gly Lys Phe Glu Phe Ser Arg Lys Asp Leu Ile Gly His Gly
 10              15                  20                  25 gcc ttc gcg gtg gtc ttc aag ggt cga cac cgc gag aag cac gac ctg        510
Ala Phe Ala Val Val Phe Lys Gly Arg His Arg Glu Lys His Asp Leu
                 30                  35                  40 gag gtg gcc gtc aaa tgc att aac aag aag aac ctt gcc aag tcc caa        558
Glu Val Ala Val Lys Cys Ile Asn Lys Lys Asn Leu Ala Lys Ser Gln
                 45                  50                  55 aca ctg ctg gga aag gaa atc aaa atc ctg aag gaa cta aag cac gaa        606
Thr Leu Leu Gly Lys Glu Ile Lys Ile Leu Lys Glu Leu Lys His Glu
         60                  65                  70 aac atc gtg gcg ctg tat gac ttc cag gaa atg gct aat tct gtc tac        654
Asn Ile Val Ala Leu Tyr Asp Phe Gln Glu Met Ala Asn Ser Val Tyr
 75                  80                  85 ctg gtc atg gag tat tgt aat ggt gga gac ctg gct gac tac ctg cac        702
Leu Val Met Glu Tyr Cys Asn Gly Gly Asp Leu Ala Asp Tyr Leu His
 90                  95                 100                 105 act atg cgc aca ctg agt gaa gac act gtc agg ctt ttc cta cag cag        750
Thr Met Arg Thr Leu Ser Glu Asp Thr Val Arg Leu Phe Leu Gln Gln
                110                 115                 120 atc gct ggc gcc atg cgg ctg ctg cac agc aag ggc atc atc cac cgg        798
Ile Ala Gly Ala Met Arg Leu Leu His Ser Lys Gly Ile Ile His Arg
                125                 130                 135 gac ctg aag ccc cag aac atc ctg ctg tcc aat cct ggg ggc cgc cgg        846
Asp Leu Lys Pro Gln Asn Ile Leu Leu Ser Asn Pro Gly Gly Arg Arg
            140                 145                 150 gcc aac ccc agc aac atc cga gtc aag att gct gac ttt gga ttc gct        894
Ala Asn Pro Ser Asn Ile Arg Val Lys Ile Ala Asp Phe Gly Phe Ala
    155                 160                 165 cgg tac ctc cag agc aac atg atg gcg gcc aca ctc tgt ggt tct cct        942
Arg Tyr Leu Gln Ser Asn Met Met Ala Ala Thr Leu Cys Gly Ser Pro
170                 175                 180                 185 atg tac atg gct cct gag gtc att atg tcc cag cac tac gat gga aag        990
Met Tyr Met Ala Pro Glu Val Ile Met Ser Gln His Tyr Asp Gly Lys
                190                 195                 200 gct gac ctg tgg agc att ggc acc att gtc tac cag tgt ctg aca ggg       1038
Ala Asp Leu Trp Ser Ile Gly Thr Ile Val Tyr Gln Cys Leu Thr Gly
                205                 210                 215 aag gcc cct ttt cag gcc agc agc cct cag gat ttg cgc ctg ttt tat       1086
Lys Ala Pro Phe Gln Ala Ser Ser Pro Gln Asp Leu Arg Leu Phe Tyr
            220                 225                 230 gag aag aac aag aca cta gtt cct gcc atc ccc cgg gag aca tca gct       1134
Glu Lys Asn Lys Thr Leu Val Pro Ala Ile Pro Arg Glu Thr Ser Ala
    235                 240                 245 ccc ctg cgg cag ctg ctc ctg gct ctg ttg cag cgg aac cac aag gac       1182
Pro Leu Arg Gln Leu Leu Leu Ala Leu Leu Gln Arg Asn His Lys Asp
250                 255                 260                 265 cgc atg gac ttt gat gaa ttt ttc cac cac cct ttc ttg gat gcc agc       1230
Arg Met Asp Phe Asp Glu Phe Phe His His Pro Phe Leu Asp Ala Ser
                270                 275                 280 acc ccc atc aag aaa tcc cca cct gtg cct gtg ccc tca tat cca agc       1278
Thr Pro Ile Lys Lys Ser Pro Pro Val Pro Val Pro Ser Tyr Pro Ser
            285                 290                 295
```

```
tca ggg tct ggc agc agc tcc agc agc agc tct gcc tcc cac ctg gcc    1326
Ser Gly Ser Gly Ser Ser Ser Ser Ser Ser Ala Ser His Leu Ala
            300                 305                 310 tct cca ccg tcc ctg ggg gag atg cca cag cta cag aag acc ctt acc    1374
Ser Pro Pro Ser Leu Gly Glu Met Pro Gln Leu Gln Lys Thr Leu Thr
    315                 320                 325 tcc cca gcc gat gct gct ggc ttt ctt cag ggc tcc cgg gac tct ggt    1422
Ser Pro Ala Asp Ala Ala Gly Phe Leu Gln Gly Ser Arg Asp Ser Gly
330                 335                 340                 345 ggc agc agc aaa gac tcc tgt gac aca gat gac ttt gtc atg gtc cca    1470
Gly Ser Ser Lys Asp Ser Cys Asp Thr Asp Asp Phe Val Met Val Pro
                350                 355                 360 gcc cag ttt cca ggt gat cta gtt gct gag gca gcc agt gcc aag ccc    1518
Ala Gln Phe Pro Gly Asp Leu Val Ala Glu Ala Ala Ser Ala Lys Pro
            365                 370                 375 cca cct gat agc ctg ctg tgt agt ggg agc tca ttg gtg gcc tct gct    1566
Pro Pro Asp Ser Leu Leu Cys Ser Gly Ser Ser Leu Val Ala Ser Ala
        380                 385                 390 ggc cta gag agc cac ggc cgt acc ccc tct ccc tct ccg acc tgc agc    1614
Gly Leu Glu Ser His Gly Arg Thr Pro Ser Pro Ser Pro Thr Cys Ser
    395                 400                 405 agc tct ccc agc ccc tct ggc cgg cct ggc ccc ttc tcc agc aac agg    1662
Ser Ser Pro Ser Pro Ser Gly Arg Pro Gly Pro Phe Ser Ser Asn Arg
410                 415                 420                 425 tac ggt gcc tcg gtc ccc att cct gtc ccc act cag gtg cac aat tac    1710
Tyr Gly Ala Ser Val Pro Ile Pro Val Pro Thr Gln Val His Asn Tyr
                430                 435                 440 cag cgc atc gag caa aac ctg caa tcg ccc act caa cag cag aca gcc    1758
Gln Arg Ile Glu Gln Asn Leu Gln Ser Pro Thr Gln Gln Gln Thr Ala
            445                 450                 455 cgg tcc tct gcc atc cga agg tca ggg agc acc acc ccc ctg ggc ttt    1806
Arg Ser Ser Ala Ile Arg Arg Ser Gly Ser Thr Thr Pro Leu Gly Phe
        460                 465                 470 ggc cgg gcc agc cca tca ccc ccc tcc cac acc gat ggg gcc atg ctg    1854
Gly Arg Ala Ser Pro Ser Pro Pro Ser His Thr Asp Gly Ala Met Leu
    475                 480                 485 gcc agg aag ctg tca ctt gga ggt ggc cgt ccc tac aca cct tct ccc    1902
Ala Arg Lys Leu Ser Leu Gly Gly Gly Arg Pro Tyr Thr Pro Ser Pro
490                 495                 500                 505 caa gtg gga acc atc cca gag cga ccc agc tgg agc aga gtg ccc tcc    1950
Gln Val Gly Thr Ile Pro Glu Arg Pro Ser Trp Ser Arg Val Pro Ser
                510                 515                 520 cca caa gga gct gat gtg cgg gtt ggc agg tca cca cga ccc ggt tcc    1998
Pro Gln Gly Ala Asp Val Arg Val Gly Arg Ser Pro Arg Pro Gly Ser
            525                 530                 535 tct gtg cct gag cac tct cca aga acc act ggg ctg ggc tgc cgc ctg    2046
Ser Val Pro Glu His Ser Pro Arg Thr Thr Gly Leu Gly Cys Arg Leu
        540                 545                 550 cac agt gcc cct aac ctg tcc gac ttc cat gtt gtg cgt ccc aag ctg    2094
His Ser Ala Pro Asn Leu Ser Asp Phe His Val Val Arg Pro Lys Leu
    555                 560                 565 cct aag ccc cca aca gac cca ctg gga gcc acc ttt agc cca ccc cag    2142
Pro Lys Pro Pro Thr Asp Pro Leu Gly Ala Thr Phe Ser Pro Pro Gln
570                 575                 580                 585 acc agc gca ccc cag cca tgc cca ggg cta cag tct tgc cgg cca ctg    2190
Thr Ser Ala Pro Gln Pro Cys Pro Gly Leu Gln Ser Cys Arg Pro Leu
                590                 595                 600 cgt ggc tca cct aag ctg cct gac ttc cta cag cgg agt ccc cta ccc    2238
Arg Gly Ser Pro Lys Leu Pro Asp Phe Leu Gln Arg Ser Pro Leu Pro
```

|  |  |  |  |  |  |  |  |  |  |  |  |  |  |  |  |
|---|---|---|---|---|---|---|---|---|---|---|---|---|---|---|---|
|  |  | 605 |  |  |  |  | 610 |  |  |  |  | 615 |  |  |  |
| ccc | atc | cta | ggc | tct | cct | acc | aag | gcc | ggg | ccc | tcc | ttt | gac | ttc | ccc |
| Pro | Ile | Leu | Gly | Ser | Pro | Thr | Lys | Ala | Gly | Pro | Ser | Phe | Asp | Phe | Pro |
|  |  | 620 |  |  |  |  | 625 |  |  |  |  | 630 |  |  |  |

2286 aaa acc ccc agc tct cag aat ttg ctg acc ctg ttg gct agg cag ggg   2334
Lys Thr Pro Ser Ser Gln Asn Leu Leu Thr Leu Leu Ala Arg Gln Gly
            635                 640                 645 gta gta atg aca cca cct cgg aac cgt aca ctg cct gac ctc tcc gag   2382
Val Val Met Thr Pro Pro Arg Asn Arg Thr Leu Pro Asp Leu Ser Glu
650                 655                 660                 665 gcc agt cct ttc cat ggc cag cag ctg ggc tct ggc ctt cgg ccc gct   2430
Ala Ser Pro Phe His Gly Gln Gln Leu Gly Ser Gly Leu Arg Pro Ala
                670                 675                 680 gaa gac acc cgg ggt ccc ttt gga cgg tcc ttc agc acc agc cgc att   2478
Glu Asp Thr Arg Gly Pro Phe Gly Arg Ser Phe Ser Thr Ser Arg Ile
                685                 690                 695 acg gac ctg ctg ctt aag gct gca ttt ggg act cag gcc tct gac tca   2526
Thr Asp Leu Leu Leu Lys Ala Ala Phe Gly Thr Gln Ala Ser Asp Ser
            700                 705                 710 ggc agc aca gac agc cta cag gag aaa cct atg gag att gct ccc tct   2574
Gly Ser Thr Asp Ser Leu Gln Glu Lys Pro Met Glu Ile Ala Pro Ser
715                 720                 725 gct ggc ttt gga ggg act ctg cat cca gga gct cgt ggt gga ggg gcc   2622
Ala Gly Phe Gly Gly Thr Leu His Pro Gly Ala Arg Gly Gly Gly Ala
730                 735                 740                 745 agc agc cca gca cct gtg gta ttt act gta ggc tcc cca ccc agt ggt   2670
Ser Ser Pro Ala Pro Val Val Phe Thr Val Gly Ser Pro Pro Ser Gly
                750                 755                 760 gcc acc cca ccc cag agt acc cgt acc aga atg ttc tca gtg ggc tct   2718
Ala Thr Pro Pro Gln Ser Thr Arg Thr Arg Met Phe Ser Val Gly Ser
                765                 770                 775 tcc agc tcc ctg ggc tct act ggc tcc tcc tct gcc cgc cac tta gtg   2766
Ser Ser Ser Leu Gly Ser Thr Gly Ser Ser Ser Ala Arg His Leu Val
            780                 785                 790 cct ggg gcc tgt gga gag gcc ccg gag ctt tct gcc cca ggc cac tgc   2814
Pro Gly Ala Cys Gly Glu Ala Pro Glu Leu Ser Ala Pro Gly His Cys
795                 800                 805 tgt agc ctt gct gac ccc ctt gct gcc aac ttg gag ggg gct gtg acc   2862
Cys Ser Leu Ala Asp Pro Leu Ala Ala Asn Leu Glu Gly Ala Val Thr
810                 815                 820                 825 ttc gag gct cct gac ctc cca gag gag acc ctc atg gag caa gag cac   2910
Phe Glu Ala Pro Asp Leu Pro Glu Glu Thr Leu Met Glu Gln Glu His
                830                 835                 840 acg gaa acc cta cac agt ctg cgc ttc aca cta gcg ttt gca cag caa   2958
Thr Glu Thr Leu His Ser Leu Arg Phe Thr Leu Ala Phe Ala Gln Gln
            845                 850                 855 gtt ctg gag att gca gcc ctg aag gga agt gcc agt gag gcc gcc ggt   3006
Val Leu Glu Ile Ala Ala Leu Lys Gly Ser Ala Ser Glu Ala Ala Gly
        860                 865                 870 ggc cct gag tac cag ctc cag gaa agt gtg gtg gct gac cag atc agt   3054
Gly Pro Glu Tyr Gln Leu Gln Glu Ser Val Val Ala Asp Gln Ile Ser
    875                 880                 885 cag ttg agc cga gag tgg ggc ttt gca gag caa ctg gtt ctg tac ttg   3102
Gln Leu Ser Arg Glu Trp Gly Phe Ala Glu Gln Leu Val Leu Tyr Leu
890                 895                 900                 905 aag gtg gct gag ctg ctg tcc tca ggc cta cag act gcc att gac cag   3150
Lys Val Ala Glu Leu Leu Ser Ser Gly Leu Gln Thr Ala Ile Asp Gln
                910                 915                 920 att cga gct ggc aaa ctc tgc ctt tca tct act gtg aag cag gtg gta   3198

```
Ile Arg Ala Gly Lys Leu Cys Leu Ser Ser Thr Val Lys Gln Val Val
            925                 930                 935 cgc aga cta aat gag ctg tac aag gcc agc gtg gta tcc tgc cag ggc    3246
Arg Arg Leu Asn Glu Leu Tyr Lys Ala Ser Val Val Ser Cys Gln Gly
            940                 945                 950 ctc agc ttg cga ctt cag cgc ttc ttt ctg gac aaa caa cgg ctg ctg    3294
Leu Ser Leu Arg Leu Gln Arg Phe Phe Leu Asp Lys Gln Arg Leu Leu
            955                 960                 965 gac ggg atc cat ggt gtc act gca gag cgg ctc atc ctc agc cat gct    3342
Asp Gly Ile His Gly Val Thr Ala Glu Arg Leu Ile Leu Ser His Ala
970                 975                 980                 985 gtg caa atg gta caa tca gct gcc ctt gat gag atg ttc cag cac cga    3390
Val Gln Met Val Gln Ser Ala Ala Leu Asp Glu Met Phe Gln His Arg
                990                 995                 1000 gag ggc tgt gta ccg aga tat cac aaa gcc ctg cta ttg ctg gag ggg    3438
Glu Gly Cys Val Pro Arg Tyr His Lys Ala Leu Leu Leu Leu Glu Gly
                1005                1010                1015 ttg cag cac act ctc acg gac cag gca gac att gag aac att gcc aaa    3486
Leu Gln His Thr Leu Thr Asp Gln Ala Asp Ile Glu Asn Ile Ala Lys
                1020                1025                1030 tgc aag ctg tgc att gag agg aga ctc tcg gcc ctg ctg agt ggt gtc    3534
Cys Lys Leu Cys Ile Glu Arg Arg Leu Ser Ala Leu Leu Ser Gly Val
                1035                1040                1045 tat gcc tgactacctg ctgccaacct gcagggtagg gtctgagacc tggcagactg     3590
Tyr Ala
1050 tcctcaacac tgatcagatc cgatggtgct gagactgctg ccagccaact ccagcaggga  3650 tgctccacag tggacctgtg cagactggtg caactcttgc ttcctagact gccagtctct  3710 gctggcaggt agacatcaga gtgccagggg tcccttgccc actgggacag gagtttctga  3770 acatattctt cctagctggc tccctggcaa gcaggtatgg tgccgagaag tgcacctgc   3830 cacctgaaga gcccatggca gccctgtgtc aggcaagggc ctgagaccgt tgctgactcc  3890 aagccaaagc aagctttccc tcacagttca cttgccccat tgcttgtcca agaaaaaagg  3950 gtatggtctt ctggccccct gttctctcta ggaactccgg aattc                 3995

<210> SEQ ID NO 14
<211> LENGTH: 1051
<212> TYPE: PRT
<213> ORGANISM: Mus musculus

<400> SEQUENCE: 14

Met Glu Pro Gly Arg Gly Gly Val Glu Thr Val Gly Lys Phe Glu Phe
1               5                   10                  15

Ser Arg Lys Asp Leu Ile Gly His Gly Ala Phe Ala Val Val Phe Lys
                20                  25                  30

Gly Arg His Arg Glu Lys His Asp Leu Glu Val Ala Val Lys Cys Ile
            35                  40                  45

Asn Lys Lys Asn Leu Ala Lys Ser Gln Thr Leu Leu Gly Lys Glu Ile
        50                  55                  60

Lys Ile Leu Lys Glu Leu Lys His Glu Asn Ile Val Ala Leu Tyr Asp
65                  70                  75                  80

Phe Gln Glu Met Ala Asn Ser Val Tyr Leu Val Met Glu Tyr Cys Asn
                85                  90                  95

Gly Gly Asp Leu Ala Asp Tyr Leu His Thr Met Arg Thr Leu Ser Glu
                100                 105                 110

Asp Thr Val Arg Leu Phe Leu Gln Gln Ile Ala Gly Ala Met Arg Leu
```

```
            115                 120                 125
Leu His Ser Lys Gly Ile Ile His Arg Asp Leu Lys Pro Gln Asn Ile
    130                 135                 140

Leu Leu Ser Asn Pro Gly Gly Arg Arg Ala Asn Pro Ser Asn Ile Arg
145                 150                 155                 160

Val Lys Ile Ala Asp Phe Gly Phe Ala Arg Tyr Leu Gln Ser Asn Met
                165                 170                 175

Met Ala Ala Thr Leu Cys Gly Ser Pro Met Tyr Met Ala Pro Glu Val
            180                 185                 190

Ile Met Ser Gln His Tyr Asp Gly Lys Ala Asp Leu Trp Ser Ile Gly
        195                 200                 205

Thr Ile Val Tyr Gln Cys Leu Thr Gly Lys Ala Pro Phe Gln Ala Ser
    210                 215                 220

Ser Pro Gln Asp Leu Arg Leu Phe Tyr Glu Lys Asn Lys Thr Leu Val
225                 230                 235                 240

Pro Ala Ile Pro Arg Glu Thr Ser Ala Pro Leu Arg Gln Leu Leu Leu
                245                 250                 255

Ala Leu Leu Gln Arg Asn His Lys Asp Arg Met Asp Phe Asp Glu Phe
            260                 265                 270

Phe His His Pro Phe Leu Asp Ala Ser Thr Pro Ile Lys Lys Ser Pro
        275                 280                 285

Pro Val Pro Val Pro Ser Tyr Pro Ser Ser Gly Ser Gly Ser Ser Ser
    290                 295                 300

Ser Ser Ser Ser Ala Ser His Leu Ala Ser Pro Pro Ser Leu Gly Glu
305                 310                 315                 320

Met Pro Gln Leu Gln Lys Thr Leu Thr Ser Pro Ala Asp Ala Ala Gly
                325                 330                 335

Phe Leu Gln Gly Ser Arg Asp Ser Gly Gly Ser Ser Lys Asp Ser Cys
            340                 345                 350

Asp Thr Asp Asp Phe Val Met Val Pro Ala Gln Phe Pro Gly Asp Leu
        355                 360                 365

Val Ala Glu Ala Ala Ser Ala Lys Pro Pro Asp Ser Leu Leu Cys
    370                 375                 380

Ser Gly Ser Ser Leu Val Ala Ser Ala Gly Leu Glu Ser His Gly Arg
385                 390                 395                 400

Thr Pro Ser Pro Ser Pro Thr Cys Ser Ser Ser Pro Ser Pro Ser Gly
                405                 410                 415

Arg Pro Gly Pro Phe Ser Ser Asn Arg Tyr Gly Ala Ser Val Pro Ile
            420                 425                 430

Pro Val Pro Thr Gln Val His Asn Tyr Gln Arg Ile Glu Gln Asn Leu
        435                 440                 445

Gln Ser Pro Thr Gln Gln Thr Ala Arg Ser Ser Ala Ile Arg Arg
    450                 455                 460

Ser Gly Ser Thr Thr Pro Leu Gly Phe Gly Arg Ala Ser Pro Ser Pro
465                 470                 475                 480

Pro Ser His Thr Asp Gly Ala Met Leu Ala Arg Lys Leu Ser Leu Gly
                485                 490                 495

Gly Gly Arg Pro Tyr Thr Pro Ser Pro Gln Val Gly Thr Ile Pro Glu
            500                 505                 510

Arg Pro Ser Trp Ser Arg Val Pro Ser Pro Gln Gly Ala Asp Val Arg
        515                 520                 525

Val Gly Arg Ser Pro Arg Pro Gly Ser Ser Val Pro Glu His Ser Pro
    530                 535                 540
```

-continued

```
Arg Thr Thr Gly Leu Gly Cys Arg Leu His Ser Ala Pro Asn Leu Ser
545                 550                 555                 560

Asp Phe His Val Val Arg Pro Lys Leu Pro Lys Pro Pro Thr Asp Pro
                565                 570                 575

Leu Gly Ala Thr Phe Ser Pro Pro Gln Thr Ser Ala Pro Gln Pro Cys
                580                 585                 590

Pro Gly Leu Gln Ser Cys Arg Pro Leu Arg Gly Ser Pro Lys Leu Pro
                595                 600                 605

Asp Phe Leu Gln Arg Ser Pro Leu Pro Pro Ile Leu Gly Ser Pro Thr
            610                 615                 620

Lys Ala Gly Pro Ser Phe Asp Phe Pro Lys Thr Pro Ser Ser Gln Asn
625                 630                 635                 640

Leu Leu Thr Leu Leu Ala Arg Gln Gly Val Val Met Thr Pro Pro Arg
                645                 650                 655

Asn Arg Thr Leu Pro Asp Leu Ser Glu Ala Ser Pro Phe His Gly Gln
                660                 665                 670

Gln Leu Gly Ser Gly Leu Arg Pro Ala Glu Asp Thr Arg Gly Pro Phe
                675                 680                 685

Gly Arg Ser Phe Ser Thr Ser Arg Ile Thr Asp Leu Leu Lys Ala
            690                 695                 700

Ala Phe Gly Thr Gln Ala Ser Asp Ser Gly Ser Thr Asp Ser Leu Gln
705                 710                 715                 720

Glu Lys Pro Met Glu Ile Ala Pro Ser Ala Gly Phe Gly Gly Thr Leu
                725                 730                 735

His Pro Gly Ala Arg Gly Gly Ala Ser Ser Pro Ala Pro Val Val
                740                 745                 750

Phe Thr Val Gly Ser Pro Pro Ser Gly Ala Thr Pro Pro Gln Ser Thr
                755                 760                 765

Arg Thr Arg Met Phe Ser Val Gly Ser Ser Ser Ser Leu Gly Ser Thr
770                 775                 780

Gly Ser Ser Ser Ala Arg His Leu Val Pro Gly Ala Cys Gly Glu Ala
785                 790                 795                 800

Pro Glu Leu Ser Ala Pro Gly His Cys Cys Ser Leu Ala Asp Pro Leu
                805                 810                 815

Ala Ala Asn Leu Glu Gly Ala Val Thr Phe Glu Ala Pro Asp Leu Pro
                820                 825                 830

Glu Glu Thr Leu Met Glu Gln Glu His Thr Glu Thr Leu His Ser Leu
                835                 840                 845

Arg Phe Thr Leu Ala Phe Ala Gln Gln Val Leu Glu Ile Ala Ala Leu
850                 855                 860

Lys Gly Ser Ala Ser Glu Ala Ala Gly Gly Pro Glu Tyr Gln Leu Gln
865                 870                 875                 880

Glu Ser Val Val Ala Asp Gln Ile Ser Gln Leu Ser Arg Glu Trp Gly
                885                 890                 895

Phe Ala Glu Gln Leu Val Leu Tyr Leu Lys Val Ala Glu Leu Leu Ser
                900                 905                 910

Ser Gly Leu Gln Thr Ala Ile Asp Gln Ile Arg Ala Gly Lys Leu Cys
                915                 920                 925

Leu Ser Ser Thr Val Lys Gln Val Val Arg Arg Leu Asn Glu Leu Tyr
                930                 935                 940

Lys Ala Ser Val Val Ser Cys Gln Gly Leu Ser Leu Arg Leu Gln Arg
945                 950                 955                 960
```

```
Phe Phe Leu Asp Lys Gln Arg Leu Leu Asp Gly Ile His Gly Val Thr
                965                 970                 975
Ala Glu Arg Leu Ile Leu Ser His Ala Val Gln Met Val Gln Ser Ala
                980                 985                 990
Ala Leu Asp Glu Met Phe Gln His Arg Glu Gly Cys Val Pro Arg Tyr
                995                1000                1005
His Lys Ala Leu Leu Leu Glu Gly Leu Gln His Thr Leu Thr Asp
       1010                1015                1020
Gln Ala Asp Ile Glu Asn Ile Ala Lys Cys Lys Leu Cys Ile Glu Arg
1025                1030                1035                1040
Arg Leu Ser Ala Leu Leu Ser Gly Val Tyr Ala
                1045                1050

<210> SEQ ID NO 15
<211> LENGTH: 5228
<212> TYPE: DNA
<213> ORGANISM: Homo sapiens
<220> FEATURE:
<221> NAME/KEY: CDS
<222> LOCATION: (269)...(3418)

<400> SEQUENCE: 15
ggatccggat tcggattagc agcccgggaa gagtgccgtg gcacaggcgc cggagggagc      60
gcgaccctcg gaccccgcct ggcccgcggg gctgggaccc ggccccggcc tgcccgatgg     120
ggcgcgcggc cccggagatg cgccctcgcc cggccccgcg ccccggcccc gcgcccccg      180 gcccgcccgc cccggcccgc gcctccgcct gagtccccg  cgccttggcc cgccacccc      240 cgccccgcgc cccggcccg  cctgcgcc atg gag ccc ggc cgc ggc ggc aca        292
                               Met Glu Pro Gly Arg Gly Gly Thr
                                 1               5 gag acc gtg ggc aag ttc gag ttc tcc cgc aag gac ctg atc ggc cac      340
Glu Thr Val Gly Lys Phe Glu Phe Ser Arg Lys Asp Leu Ile Gly His
         10                  15                  20 ggc gcc ttc gcg gtg gtc ttc aag ggc cgc cac cgc gag aag cac gat      388
Gly Ala Phe Ala Val Val Phe Lys Gly Arg His Arg Glu Lys His Asp
 25                  30                  35                  40 ttg gag gtc gcc gtc aag tgc att aac aag aag aac ctc gcc aag tct      436
Leu Glu Val Ala Val Lys Cys Ile Asn Lys Lys Asn Leu Ala Lys Ser
                 45                  50                  55 cag acg ctg ctg ggg aag gaa atc aaa atc ctg aag gaa ctg aaa cat      484
Gln Thr Leu Leu Gly Lys Glu Ile Lys Ile Leu Lys Glu Leu Lys His
             60                  65                  70 gaa aac atc gtg gcc ctg tac gac ttc cag gaa atg gct aat tct gtc      532
Glu Asn Ile Val Ala Leu Tyr Asp Phe Gln Glu Met Ala Asn Ser Val
         75                  80                  85 tac ctg gtt atg gag tac tgc aac ggt ggg gac ctg gcc gac tac ctg      580
Tyr Leu Val Met Glu Tyr Cys Asn Gly Gly Asp Leu Ala Asp Tyr Leu
     90                  95                 100 cac gcc atg cgc acg ctg agc gag gac acc atc agg ctc ttc ctg cag      628
His Ala Met Arg Thr Leu Ser Glu Asp Thr Ile Arg Leu Phe Leu Gln
105                 110                 115                 120 cag atc gcg ggc gcc atg cgg ctt ctg cac agc aaa ggc atc atc cac      676
Gln Ile Ala Gly Ala Met Arg Leu Leu His Ser Lys Gly Ile Ile His
                125                 130                 135 cgc gac ctg aaa ccg cag aac atc ctg ctg tcc aac ccc gcc ggc cgc      724
Arg Asp Leu Lys Pro Gln Asn Ile Leu Leu Ser Asn Pro Ala Gly Arg
            140                 145                 150 cgc gcc aac ccc aac agc atc cgc gtc aag atc gct gac ttc ggc ttc      772
Arg Ala Asn Pro Asn Ser Ile Arg Val Lys Ile Ala Asp Phe Gly Phe
```

-continued

|  |  |  |  |
|---|---|---|---|
| 155 | 160 | 165 | |
| gcg cgg tac ctc cag agc aac atg atg gcg gcc aca ctc tgc ggc tcc<br>Ala Arg Tyr Leu Gln Ser Asn Met Met Ala Ala Thr Leu Cys Gly Ser<br>170 175 180 | | | 820 |
| ccc atg tac atg gcc ccc gag gtc atc atg tcc cag cac tac gac ggg<br>Pro Met Tyr Met Ala Pro Glu Val Ile Met Ser Gln His Tyr Asp Gly<br>185 190 195 200 | | | 868 |
| aag gcg gac ctg tgg agc atc ggc acc atc gtc tac cag tgc ctg acg<br>Lys Ala Asp Leu Trp Ser Ile Gly Thr Ile Val Tyr Gln Cys Leu Thr<br>205 210 215 | | | 916 |
| ggg aag gcg ccc ttc cag gcc agc agc ccc cag gac ctg cgc ctg ttc<br>Gly Lys Ala Pro Phe Gln Ala Ser Ser Pro Gln Asp Leu Arg Leu Phe<br>220 225 230 | | | 964 |
| tac gag aag aac aag acg ttg gtc ccc acc atc ccc cgg gag acc tcg<br>Tyr Glu Lys Asn Lys Thr Leu Val Pro Thr Ile Pro Arg Glu Thr Ser<br>235 240 245 | | | 1012 |
| gcc ccg ctg cgg cag ctg ctc ctg gcc cta ctg caa cgc aac cac aag<br>Ala Pro Leu Arg Gln Leu Leu Leu Ala Leu Leu Gln Arg Asn His Lys<br>250 255 260 | | | 1060 |
| gac cgc atg gac ttc gat gag ttt ttt cat cac cct ttc ctc gat gcc<br>Asp Arg Met Asp Phe Asp Glu Phe Phe His His Pro Phe Leu Asp Ala<br>265 270 275 280 | | | 1108 |
| agc ccc tcg gtc agg aaa tcc cca ccc gtg cct gtg ccc tcg tac cca<br>Ser Pro Ser Val Arg Lys Ser Pro Pro Val Pro Val Pro Ser Tyr Pro<br>285 290 295 | | | 1156 |
| agc tcg ggg tcc ggc agc agc tcc agc agc agc tcc acc tcc cac ctg<br>Ser Ser Gly Ser Gly Ser Ser Ser Ser Ser Ser Thr Ser His Leu<br>300 305 310 | | | 1204 |
| gcc tcc ccg ccg tcc ctg ggc gag atg cag cag ctg cag aag acc ctg<br>Ala Ser Pro Pro Ser Leu Gly Glu Met Gln Gln Leu Gln Lys Thr Leu<br>315 320 325 | | | 1252 |
| gcc tcc ccg gct gac acc gct ggc ttc ctg cac agc tcc cgg gac tct<br>Ala Ser Pro Ala Asp Thr Ala Gly Phe Leu His Ser Ser Arg Asp Ser<br>330 335 340 | | | 1300 |
| ggt ggc agc aag gac tct tcc tgt gac aca gac gac ttc gtc atg gtc<br>Gly Gly Ser Lys Asp Ser Ser Cys Asp Thr Asp Asp Phe Val Met Val<br>345 350 355 360 | | | 1348 |
| ccc gcg cag ttt cca ggt gac ctg gtg gct gag gcg ccc agt gcc aaa<br>Pro Ala Gln Phe Pro Gly Asp Leu Val Ala Glu Ala Pro Ser Ala Lys<br>365 370 375 | | | 1396 |
| ccc ccg cca gac agc ctg atg tgc agt ggg agc tca ctg gtg gcc tct<br>Pro Pro Pro Asp Ser Leu Met Cys Ser Gly Ser Ser Leu Val Ala Ser<br>380 385 390 | | | 1444 |
| gcg ggc ttg gag agc cac ggc cgg acc cca tct cca tcc cca ccc tgc<br>Ala Gly Leu Glu Ser His Gly Arg Thr Pro Ser Pro Ser Pro Pro Cys<br>395 400 405 | | | 1492 |
| agc agc tcc ccc agt ccc tca ggc cgg gct ggc ccg ttc tcc agc agc<br>Ser Ser Ser Pro Ser Pro Ser Gly Arg Ala Gly Pro Phe Ser Ser Ser<br>410 415 420 | | | 1540 |
| agg tgc ggc gcc tct gtc ccc atc cca gtc ccc acg cag gtg cag aac<br>Arg Cys Gly Ala Ser Val Pro Ile Pro Val Pro Thr Gln Val Gln Asn<br>425 430 435 440 | | | 1588 |
| tac cag cgc att gag cga aac ctg cag tca ccc acc cag ttc caa aca<br>Tyr Gln Arg Ile Glu Arg Asn Leu Gln Ser Pro Thr Gln Phe Gln Thr<br>445 450 455 | | | 1636 |
| cct cgg tcc tct gcc atc cgc agg tca ggc agc acc agc ccc ctg ggc<br>Pro Arg Ser Ser Ala Ile Arg Arg Ser Gly Ser Thr Ser Pro Leu Gly<br>460 465 470 | | | 1684 |
| ttt gca agg gcc agc ccc tcg ccc cct gcc cac gct gag cat gga ggc<br> | | | 1732 |

```
                    Phe Ala Arg Ala Ser Pro Ser Pro Ala His Ala Glu His Gly Gly
                        475                 480                 485 gtc ctg gcc agg aag atg tct ctg ggt gga ggc cgg ccc tac acg cca               1780
Val Leu Ala Arg Lys Met Ser Leu Gly Gly Gly Arg Pro Tyr Thr Pro
        490                 495                 500 tct cct caa gtt gga acc atc cct gag cgg cca ggc tgg agc ggg acg               1828
Ser Pro Gln Val Gly Thr Ile Pro Glu Arg Pro Gly Trp Ser Gly Thr
505                 510                 515                 520 ccc tcc cca cag gga gct gag atg cgg ggt ggc agg tcc cct cgt cca               1876
Pro Ser Pro Gln Gly Ala Glu Met Arg Gly Gly Arg Ser Pro Arg Pro
                525                 530                 535 ggc tcc tct gca ccc gag cac tct ccc cgc act tcc ggg ctg ggc tgc               1924
Gly Ser Ser Ala Pro Glu His Ser Pro Arg Thr Ser Gly Leu Gly Cys
        540                 545                 550 cgc ctg cac agc gcc ccc aac ctg tct gac ttg cac gtc gtc cgc ccc               1972
Arg Leu His Ser Ala Pro Asn Leu Ser Asp Leu His Val Val Arg Pro
                555                 560                 565 aag ctg ccc aaa ccc ccc acg gac ccc ctg gga gct gtg ttc agc cca               2020
Lys Leu Pro Lys Pro Pro Thr Asp Pro Leu Gly Ala Val Phe Ser Pro
        570                 575                 580 cca cag gcc agc cct ccc cag ccg tcc cac ggc ctg cag tcc tgc cgg               2068
Pro Gln Ala Ser Pro Pro Gln Pro Ser His Gly Leu Gln Ser Cys Arg
585                 590                 595                 600 aac ctg cgg ggc tca ccc aag ctg ccc gac ttc ctg cag cga aac ccc               2116
Asn Leu Arg Gly Ser Pro Lys Leu Pro Asp Phe Leu Gln Arg Asn Pro
                605                 610                 615 ctg ccc ccc atc ctg ggc tcc ccc acc aag gct gtg ccc tcc ttt gac               2164
Leu Pro Pro Ile Leu Gly Ser Pro Thr Lys Ala Val Pro Ser Phe Asp
        620                 625                 630 ttc ccg aag acc ccc agc tcc cag aac ctg ctg gcc ctc cta gcc cgg               2212
Phe Pro Lys Thr Pro Ser Ser Gln Asn Leu Leu Ala Leu Leu Ala Arg
                635                 640                 645 cag ggc gtg gtg atg acg ccc cct cga aac cgg acg ctg ccc gac ctc               2260
Gln Gly Val Val Met Thr Pro Pro Arg Asn Arg Thr Leu Pro Asp Leu
        650                 655                 660 tcg gag gtg gga ccc ttc cat ggt cag ccg ttg ggc cct ggc ctg cgg               2308
Ser Glu Val Gly Pro Phe His Gly Gln Pro Leu Gly Pro Gly Leu Arg
665                 670                 675                 680 cca ggc gag gac ccc aag ggc ccc ttt ggc cgg tct ttc agc acc agc               2356
Pro Gly Glu Asp Pro Lys Gly Pro Phe Gly Arg Ser Phe Ser Thr Ser
                685                 690                 695 cgc ctc act gac ctg ctc ctt aag gcg gcg ttt ggg aca caa gcc ccg               2404
Arg Leu Thr Asp Leu Leu Leu Lys Ala Ala Phe Gly Thr Gln Ala Pro
        700                 705                 710 gac ccg ggc agc acg gag agc ctg cag gag aag ccc atg gag atc gca               2452
Asp Pro Gly Ser Thr Glu Ser Leu Gln Glu Lys Pro Met Glu Ile Ala
                715                 720                 725 ccc tca gct ggc ttt gga ggg agc ctg cac cca gga gcc cgt gct ggg               2500
Pro Ser Ala Gly Phe Gly Gly Ser Leu His Pro Gly Ala Arg Ala Gly
730                 735                 740 ggc acc agc agc ccc tcc ccg gtg gtc ttc acc gtg ggc tct ccc ccg               2548
Gly Thr Ser Ser Pro Ser Pro Val Val Phe Thr Val Gly Ser Pro Pro
        745                 750                 755                 760 agc ggg agc acg ccc ccc cag ggc ccc cgc acc agg atg ttc tca gcg               2596
Ser Gly Ser Thr Pro Pro Gln Gly Pro Arg Thr Arg Met Phe Ser Ala
                765                 770                 775 ggc ccc act ggc tct gcc agc tct tct gcc cgc cac ctg gtg cct ggg               2644
Gly Pro Thr Gly Ser Ala Ser Ser Ala Arg His Leu Val Pro Gly
        780                 785                 790
```

-continued

| | | |
|---|---|---|
| ccc tgc agc gag gcc cca gcc cct gag ctc cct gct cca gga cac ggc<br>Pro Cys Ser Glu Ala Pro Ala Pro Glu Leu Pro Ala Pro Gly His Gly<br>795                        800                      805 | 2692 |
| tgc agc ttt gcc gac ccc att gct gcg aac ctg gag ggg gct gtg acc<br>Cys Ser Phe Ala Asp Pro Ile Ala Ala Asn Leu Glu Gly Ala Val Thr<br>810                        815                      820 | 2740 |
| ttc gag gcc ccc gac ctc cct gag gag acc ctc atg gag caa gag cac<br>Phe Glu Ala Pro Asp Leu Pro Glu Glu Thr Leu Met Glu Gln Glu His<br>825                        830                      835                      840 | 2788 |
| acg gag atc ctg cgt ggc ctg cgc ttc acg ctg ctg ttc gtg cag cac<br>Thr Glu Ile Leu Arg Gly Leu Arg Phe Thr Leu Leu Phe Val Gln His<br>845                        850                      855 | 2836 |
| gtc ctg gag atc gca gcc ctg aag ggc agc gcc agt gag gcg gcg ggg<br>Val Leu Glu Ile Ala Ala Leu Lys Gly Ser Ala Ser Glu Ala Ala Gly<br>860                        865                      870 | 2884 |
| ggc cct gag tac cag ctg cag gag agt gtg gtg gcc gac cag atc agc<br>Gly Pro Glu Tyr Gln Leu Gln Glu Ser Val Val Ala Asp Gln Ile Ser<br>875                        880                      885 | 2932 |
| ctg ctg agc cga gaa tgg ggc ttc gcg gaa cag ctg gtg ctg tac ctg<br>Leu Leu Ser Arg Glu Trp Gly Phe Ala Glu Gln Leu Val Leu Tyr Leu<br>890                        895                      900 | 2980 |
| aag gtg gcc gag cta ctg tcc tcc ggc ctg caa agt gcc atc gac cag<br>Lys Val Ala Glu Leu Leu Ser Ser Gly Leu Gln Ser Ala Ile Asp Gln<br>905                        910                      915                      920 | 3028 |
| atc cgg gcc ggc aag ctc tgc ctg tcg tcc act gtg aag cag gtg gtg<br>Ile Arg Ala Gly Lys Leu Cys Leu Ser Ser Thr Val Lys Gln Val Val<br>925                        930                      935 | 3076 |
| cgc agg ctg aat gag ctg tac aag gcc agc gtg gtg tcc tgc cag ggc<br>Arg Arg Leu Asn Glu Leu Tyr Lys Ala Ser Val Val Ser Cys Gln Gly<br>940                        945                      950 | 3124 |
| ctg agc ctg cgg ctg cag cgc ttc ttc ctg gac aag cag cgg ctc ctg<br>Leu Ser Leu Arg Leu Gln Arg Phe Phe Leu Asp Lys Gln Arg Leu Leu<br>955                        960                      965 | 3172 |
| gac cgc att cac agc atc act gcc gag agg ctc atc ttc agc cac gct<br>Asp Arg Ile His Ser Ile Thr Ala Glu Arg Leu Ile Phe Ser His Ala<br>970                        975                      980 | 3220 |
| gtg cag atg gtg cag tcg gct gcc ctg gac gag atg ttc cag cac cgt<br>Val Gln Met Val Gln Ser Ala Ala Leu Asp Glu Met Phe Gln His Arg<br>985                        990                      995                      1000 | 3268 |
| gag ggc tgc gtc cca cgc tac cac aag gcc ctg ctg ctc ctg gag ggg<br>Glu Gly Cys Val Pro Arg Tyr His Lys Ala Leu Leu Leu Leu Glu Gly<br>1005                       1010                     1015 | 3316 |
| ctg cag cac atg ctc tcg gac cag gcc gac atc gag aac gtc acc aag<br>Leu Gln His Met Leu Ser Asp Gln Ala Asp Ile Glu Asn Val Thr Lys<br>1020                       1025                     1030 | 3364 |
| tgc aag ctg tgc att gag cgg aga ctc tcg gcg ctg ctg act ggc atc<br>Cys Lys Leu Cys Ile Glu Arg Arg Leu Ser Ala Leu Leu Thr Gly Ile<br>1035                       1040                     1045 | 3412 |
| tgt gcc tgacctttct ggcctggctg ggcccccgt cctgccgagc cctgcagagt<br>Cys Ala<br>1050 | 3468 |
| gggctctgtg tgctggctgg actcctcggg acaagcccat ggcgctgatc gctggtgctg | 3528 |
| agccctgccc tgggcccac ggacagtcag cctgccggcc tccctgcagc tcacggggca | 3588 |
| gaaccagcac atctggagcc acacagcttg gggggtgtct cccatctttt acaggtgggg | 3648 |
| atcacagaat ttctgcccct ccagctgcct ggctcagcag gcgtgggtgc caccaccctc | 3708 |
| tagccccagg gcagccccgg aggacaggca agggcctgag accactgccg actcaaagcc | 3768 |
| aaagcgagct cctgcttagg gcaggtcagc aggcactgtg cccaggaaga gcctgcggcc | 3828 |

-continued

```
tcggcgtccc ccagtctcca ggagcctctc cctccgagat acccacccag ctttgtcaat    3888
cacccaagca ctttatgcat atagagacag aacctggacc tcaccaggga ctgctgggca    3948
gcgattcctg gcagtggcct ggtgtttgta catacacata tgcagacaca tgccagggcc    4008
ccccaagccc gagcaccgga ccacgttgct gcccaggtct ggacctcagc gggagaactg    4068
gctccggggg gagtggggcc ctgcgctaga ggcagaggca gttctttgtt caagcgttcc    4128
tctggggacc ggcagcagag gcaccgtgtt ctctcagccc tggatacgtc ttgtaatctt    4188
tcacacttta ttcctaaaac gtgtcttatt tttatgcagc tcattttttc tttaaaggag    4248
aaaacttgta ggtgtttaag aattggtttt gggagggcga ggactgggcc aggttagagg    4308
cagatggcac aggggcgtgt ggcgggcggg tgaggctgct ttgcacacct gtgttggtgg    4368
ctgtcccctg ccgcccctcc ctgtggcagc agcaggacag gtgtgtgccc agcaccctcc    4428
ctacctgggc ctgaagcag atgaggggaa tacttcatgc aaagaaaaaa gtaacatgtg     4488
caaaagctcc ccgtccagct ttgacagtca gttttgatgt cagctcctcg gcagggtagg    4548
cctgatgaca gccctgtccc tccctgcctc cgccttgccc aaggccacgg agggcgtctg    4608
cagagaggcc tgccttccgg attccaggcg ggcatgccct gcaaaccccg cctgggcctc    4668
ccttggtctg cccagccctc ggttagccct gcctgaatca gtagatactt gaacgagtcc    4728
ccagtctgcg ggaggcagtg gtggggccat ggacccatgc gggggttcc agggtcacac     4788 gccacataac agacaaaaat acacacacgt gtgtttttct ttgcaatact tgaaatattg    4848
ccactgtgct tggacttaga agaagaaaat ccccgtgact tcttcctcat caccttgatg    4908
gctttattct caccttgtgg ggcatgtttg aatttattgc ttcatggccg actggaatcc    4968
tgagtcctgg gaagctggca ctgcggggat cttgcccggt gtcctggtcc tcttgcttcc    5028
gtcgcggccg catgtgcgtg tgtccaagca ggtcctgggc gcctcaactg ctgcccctgg    5088
ttgaatgttc tcttgatagt gctggaccct ttgtctattt taaagcgaat tttgtgtgat    5148
ttcctgccct ttgcgttata ttgtataata ccaacgtaag gaaataaacc tttggaattg    5208
ttgaaaaaaa aaaaaaaaa                                                 5228
```

<210> SEQ ID NO 16
<211> LENGTH: 1050
<212> TYPE: PRT
<213> ORGANISM: Homo sapiens

<400> SEQUENCE: 16

```
Met Glu Pro Gly Arg Gly Gly Thr Glu Thr Val Gly Lys Phe Glu Phe
  1               5                  10                  15

Ser Arg Lys Asp Leu Ile Gly His Gly Ala Phe Ala Val Val Phe Lys
                 20                  25                  30

Gly Arg His Arg Glu Lys His Asp Leu Glu Val Ala Val Lys Cys Ile
             35                  40                  45

Asn Lys Lys Asn Leu Ala Lys Ser Gln Thr Leu Leu Gly Lys Glu Ile
         50                  55                  60

Lys Ile Leu Lys Glu Leu Lys His Glu Asn Ile Val Ala Leu Tyr Asp
     65                  70                  75                  80

Phe Gln Glu Met Ala Asn Ser Val Tyr Leu Val Met Glu Tyr Cys Asn
                 85                  90                  95

Gly Gly Asp Leu Ala Asp Tyr Leu His Ala Met Arg Thr Leu Ser Glu
                100                 105                 110

Asp Thr Ile Arg Leu Phe Leu Gln Gln Ile Ala Gly Ala Met Arg Leu
```

-continued

```
            115                 120                 125
Leu His Ser Lys Gly Ile Ile His Arg Asp Leu Lys Pro Gln Asn Ile
    130                 135                 140
Leu Leu Ser Asn Pro Ala Gly Arg Arg Ala Asn Pro Asn Ser Ile Arg
145                 150                 155                 160
Val Lys Ile Ala Asp Phe Gly Phe Ala Arg Tyr Leu Gln Ser Asn Met
                165                 170                 175
Met Ala Ala Thr Leu Cys Gly Ser Pro Met Tyr Met Ala Pro Glu Val
                180                 185                 190
Ile Met Ser Gln His Tyr Asp Gly Lys Ala Asp Leu Trp Ser Ile Gly
            195                 200                 205
Thr Ile Val Tyr Gln Cys Leu Thr Gly Lys Ala Pro Phe Gln Ala Ser
    210                 215                 220
Ser Pro Gln Asp Leu Arg Leu Phe Tyr Glu Lys Asn Lys Thr Leu Val
225                 230                 235                 240
Pro Thr Ile Pro Arg Glu Thr Ser Ala Pro Leu Arg Gln Leu Leu Leu
                245                 250                 255
Ala Leu Leu Gln Arg Asn His Lys Asp Arg Met Asp Phe Asp Glu Phe
            260                 265                 270
Phe His His Pro Phe Leu Asp Ala Ser Pro Ser Val Arg Lys Ser Pro
    275                 280                 285
Pro Val Pro Val Pro Ser Tyr Pro Ser Ser Gly Ser Gly Ser Ser Ser
    290                 295                 300
Ser Ser Ser Ser Thr Ser His Leu Ala Ser Pro Pro Ser Leu Gly Glu
305                 310                 315                 320
Met Gln Gln Leu Gln Lys Thr Leu Ala Ser Pro Ala Asp Thr Ala Gly
                325                 330                 335
Phe Leu His Ser Ser Arg Asp Ser Gly Gly Ser Lys Asp Ser Ser Cys
            340                 345                 350
Asp Thr Asp Asp Phe Val Met Val Pro Ala Gln Phe Pro Gly Asp Leu
    355                 360                 365
Val Ala Glu Ala Pro Ser Ala Lys Pro Pro Asp Ser Leu Met Cys
    370                 375                 380
Ser Gly Ser Ser Leu Val Ala Ser Ala Gly Leu Glu Ser His Gly Arg
385                 390                 395                 400
Thr Pro Ser Pro Ser Pro Cys Ser Ser Pro Ser Pro Ser Gly
                405                 410                 415
Arg Ala Gly Pro Phe Ser Ser Arg Cys Gly Ala Ser Val Pro Ile
            420                 425                 430
Pro Val Pro Thr Gln Val Gln Asn Tyr Gln Arg Ile Glu Arg Asn Leu
    435                 440                 445
Gln Ser Pro Thr Gln Phe Gln Thr Pro Arg Ser Ser Ala Ile Arg Arg
    450                 455                 460
Ser Gly Ser Thr Ser Pro Leu Gly Phe Ala Arg Ala Ser Pro Ser Pro
465                 470                 475                 480
Pro Ala His Ala Glu His Gly Val Leu Ala Arg Lys Met Ser Leu
                485                 490                 495
Gly Gly Gly Arg Pro Tyr Thr Pro Ser Pro Gln Val Gly Thr Ile Pro
            500                 505                 510
Glu Arg Pro Gly Trp Ser Gly Thr Pro Ser Pro Gln Gly Ala Glu Met
            515                 520                 525
Arg Gly Gly Arg Ser Pro Arg Pro Gly Ser Ser Ala Pro Glu His Ser
            530                 535                 540
```

-continued

```
Pro Arg Thr Ser Gly Leu Gly Cys Arg Leu His Ser Ala Pro Asn Leu
545                 550                 555                 560

Ser Asp Leu His Val Val Arg Pro Lys Leu Pro Lys Pro Pro Thr Asp
                565                 570                 575

Pro Leu Gly Ala Val Phe Ser Pro Pro Gln Ala Ser Pro Pro Gln Pro
                580                 585                 590

Ser His Gly Leu Gln Ser Cys Arg Asn Leu Arg Gly Ser Pro Lys Leu
                595                 600                 605

Pro Asp Phe Leu Gln Arg Asn Pro Leu Pro Pro Ile Leu Gly Ser Pro
610                 615                 620

Thr Lys Ala Val Pro Ser Phe Asp Phe Pro Lys Thr Pro Ser Ser Gln
625                 630                 635                 640

Asn Leu Ala Leu Leu Ala Arg Gln Gly Val Val Met Thr Pro Pro
                645                 650                 655

Arg Asn Arg Thr Leu Pro Asp Leu Ser Glu Val Gly Pro Phe His Gly
                660                 665                 670

Gln Pro Leu Gly Pro Gly Leu Arg Pro Gly Glu Asp Pro Lys Gly Pro
                675                 680                 685

Phe Gly Arg Ser Phe Ser Thr Ser Arg Leu Thr Asp Leu Leu Leu Lys
                690                 695                 700

Ala Ala Phe Gly Thr Gln Ala Pro Asp Pro Gly Ser Thr Glu Ser Leu
705                 710                 715                 720

Gln Glu Lys Pro Met Glu Ile Ala Pro Ser Ala Gly Phe Gly Gly Ser
                725                 730                 735

Leu His Pro Gly Ala Arg Ala Gly Gly Thr Ser Ser Pro Ser Pro Val
                740                 745                 750

Val Phe Thr Val Gly Ser Pro Pro Ser Gly Ser Thr Pro Pro Gln Gly
                755                 760                 765

Pro Arg Thr Arg Met Phe Ser Ala Gly Pro Thr Gly Ser Ala Ser Ser
                770                 775                 780

Ser Ala Arg His Leu Val Pro Gly Pro Cys Ser Glu Ala Pro Ala Pro
785                 790                 795                 800

Glu Leu Pro Ala Pro Gly His Gly Cys Ser Phe Ala Asp Pro Ile Ala
                805                 810                 815

Ala Asn Leu Glu Gly Ala Val Thr Phe Glu Ala Pro Asp Leu Pro Glu
                820                 825                 830

Glu Thr Leu Met Glu Gln Glu His Thr Glu Ile Leu Arg Gly Leu Arg
                835                 840                 845

Phe Thr Leu Leu Phe Val Gln His Val Leu Glu Ile Ala Ala Leu Lys
                850                 855                 860

Gly Ser Ala Ser Glu Ala Ala Gly Gly Pro Glu Tyr Gln Leu Gln Glu
865                 870                 875                 880

Ser Val Val Ala Asp Gln Ile Ser Leu Leu Ser Arg Glu Trp Gly Phe
                885                 890                 895

Ala Glu Gln Leu Val Leu Tyr Leu Lys Val Ala Glu Leu Leu Ser Ser
                900                 905                 910

Gly Leu Gln Ser Ala Ile Asp Gln Ile Arg Ala Gly Lys Leu Cys Leu
                915                 920                 925

Ser Ser Thr Val Lys Gln Val Val Arg Arg Leu Asn Glu Leu Tyr Lys
                930                 935                 940

Ala Ser Val Val Ser Cys Gln Gly Leu Ser Leu Arg Leu Gln Arg Phe
945                 950                 955                 960
```

```
Phe Leu Asp Lys Gln Arg Leu Leu Asp Arg Ile His Ser Ile Thr Ala
                965                 970                 975
Glu Arg Leu Ile Phe Ser His Ala Val Gln Met Val Gln Ser Ala Ala
            980                 985                 990
Leu Asp Glu Met Phe Gln His Arg Glu Gly Cys Val Pro Arg Tyr His
        995                 1000                1005
Lys Ala Leu Leu Leu Glu Gly Leu Gln His Met Leu Ser Asp Gln
    1010                1015                1020
Ala Asp Ile Glu Asn Val Thr Lys Cys Lys Leu Cys Ile Glu Arg Arg
1025                1030                1035                1040
Leu Ser Ala Leu Leu Thr Gly Ile Cys Ala
                1045                1050

<210> SEQ ID NO 17
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 17
tgcccaccct agcgctctat g                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 18
attcgcatgg ctgccgcaat c                                              21

<210> SEQ ID NO 19
<211> LENGTH: 445
<212> TYPE: DNA
<213> ORGANISM: Mus musculus
<220> FEATURE:
<221> NAME/KEY: misc_feature
<222> LOCATION: (1)...(445)
<223> OTHER INFORMATION: n = A,T,C or G

<400> SEQUENCE: 19
tgcatgcctg cacgtcgact ctagaggatc tactantcat atggatttgc ccaccctacg    60
ctctatgtcc cggggcgcg gccatggaag tggtgggcga cttcgagtac tgcaagcggg   120
acctcgtggg acacggggcc ttcgctgtgg tcttccgggg gcggcaccgc cagaaaactg   180
attgggaggt ggctattaaa agtattaata aaaagaactt gtcaaaatca caattttgc    240 ttggaaagga aataaaaatc ttaaggagc ttcagcatga aaacatcgta gcgctctatg   300
atgttcagga attgcccaac tctgtctttc tggtgatgga gtattgcaat ggtggagacc   360
tggcagatta tttgcaagct aaaggaactc tgagtgaaga tactatcaga gtgtttctcc   420
atcagattgc ggcagccatg cgaat                                         445

<210> SEQ ID NO 20
<211> LENGTH: 3455
<212> TYPE: DNA
<213> ORGANISM: Mus musculus
<220> FEATURE:
<221> NAME/KEY: CDS
<222> LOCATION: (42)...(3152)
```

<400> SEQUENCE: 20

```
cgcctgccca ccctagcgtt ctatgtcccg ggggcgcggc c atg gag gtg gtg ggc       56
                                              Met Glu Val Val Gly
                                                1               5 gac ttc gag tac tgc aag cgg gac ctc gtg gga cac ggg gcc ttc gct        104
Asp Phe Glu Tyr Cys Lys Arg Asp Leu Val Gly His Gly Ala Phe Ala
             10                  15                  20 gtg gtc ttc cgg ggg cgg cac cgc cag aaa act gat tgg gag gtg gct        152
Val Val Phe Arg Gly Arg His Arg Gln Lys Thr Asp Trp Glu Val Ala
         25                  30                  35 att aaa agt att aat aaa aag aac ttg tca aaa tca caa att ctg ctt        200
Ile Lys Ser Ile Asn Lys Lys Asn Leu Ser Lys Ser Gln Ile Leu Leu
     40                  45                  50 gga aag gaa ata aaa atc tta aag gag ctt cag cat gaa aac atc gta        248
Gly Lys Glu Ile Lys Ile Leu Lys Glu Leu Gln His Glu Asn Ile Val
 55                  60                  65 gcg ctc tat gat gtt cag gaa ttg ccc aac tct gtc ttt ctg gtg atg        296
Ala Leu Tyr Asp Val Gln Glu Leu Pro Asn Ser Val Phe Leu Val Met
 70                  75                  80                  85 gag tat tgc aat ggt gga gac ctg gca gat tat ttg caa gct aaa gga        344
Glu Tyr Cys Asn Gly Gly Asp Leu Ala Asp Tyr Leu Gln Ala Lys Gly
                 90                  95                 100 act ctg agt gaa gat act atc aga gtg ttt ctc cat cag att gcg gca        392
Thr Leu Ser Glu Asp Thr Ile Arg Val Phe Leu His Gln Ile Ala Ala
            105                 110                 115 gcc atg cga atc ctg cac agc aaa ggg ata atc cac agg gat ctc aaa        440
Ala Met Arg Ile Leu His Ser Lys Gly Ile Ile His Arg Asp Leu Lys
        120                 125                 130 cca cag aat atc ctg ttg tct tat gcc aat cga agg aag tcg aat gtc        488
Pro Gln Asn Ile Leu Leu Ser Tyr Ala Asn Arg Arg Lys Ser Asn Val
    135                 140                 145 agt ggt att cgt att aaa ata gct gat ttt ggt ttc gca cgg tac cta        536
Ser Gly Ile Arg Ile Lys Ile Ala Asp Phe Gly Phe Ala Arg Tyr Leu
150                 155                 160                 165 cat agt aac aca atg gca gcg aca ctg tgt gga tcc cca atg tac atg        584
His Ser Asn Thr Met Ala Ala Thr Leu Cys Gly Ser Pro Met Tyr Met
                170                 175                 180 gct ccc gag gtt att atg tct caa cat tat gat gct aag gca gat tta        632
Ala Pro Glu Val Ile Met Ser Gln His Tyr Asp Ala Lys Ala Asp Leu
            185                 190                 195 tgg agc ata gga aca gtg atc tat caa tgc cta gtt gga aaa cca cct        680
Trp Ser Ile Gly Thr Val Ile Tyr Gln Cys Leu Val Gly Lys Pro Pro
        200                 205                 210 ttt cag gct aat agt cct cag gac cta agg atg ttt tat gaa aaa aac        728
Phe Gln Ala Asn Ser Pro Gln Asp Leu Arg Met Phe Tyr Glu Lys Asn
    215                 220                 225 agg agc tta atg cct agt att ccc aga gaa aca tca cct tac ttg gct        776
Arg Ser Leu Met Pro Ser Ile Pro Arg Glu Thr Ser Pro Tyr Leu Ala
230                 235                 240                 245 aat ctc ctt ttg ggt ttg ctt cag aga aat caa aag gat aga atg gac        824
Asn Leu Leu Leu Gly Leu Leu Gln Arg Asn Gln Lys Asp Arg Met Asp
                250                 255                 260 ttt gaa gca ttt ttc agc cat cct ttc ctt gag caa gtt cca gtt aaa        872
Phe Glu Ala Phe Phe Ser His Pro Phe Leu Glu Gln Val Pro Val Lys
            265                 270                 275 aaa tct tgc cca gtc cca gtg cct gtg tat tct ggc cct gtc cct gga        920
Lys Ser Cys Pro Val Pro Val Pro Val Tyr Ser Gly Pro Val Pro Gly
        280                 285                 290 agc tcc tgc agc agc tca cca tct tgt cgc ttt gct tct cca cca tcc        968
```

```
                                                      -continued

Ser Ser Cys Ser Ser Ser Pro Ser Cys Arg Phe Ala Ser Pro Pro Ser
    295                 300                 305 ctt cca gat atg cag cat att cag gaa gaa aac tta tcc tcc cca ccg    1016
Leu Pro Asp Met Gln His Ile Gln Glu Glu Asn Leu Ser Ser Pro Pro
310                 315                 320                 325 ttg ggt cct ccc aac tat cta cag gtg tcc aaa gac tct gcg agt aat    1064
Leu Gly Pro Pro Asn Tyr Leu Gln Val Ser Lys Asp Ser Ala Ser Asn
                330                 335                 340 agt agc aag aac tct tct tgt gac acg gat gac ttt gtt ttg gtt cca    1112
Ser Ser Lys Asn Ser Ser Cys Asp Thr Asp Asp Phe Val Leu Val Pro
            345                 350                 355 cac aac atc tcg tca gac cac tca tat gac atg cca atg ggg act acg    1160
His Asn Ile Ser Ser Asp His Ser Tyr Asp Met Pro Met Gly Thr Thr
        360                 365                 370 gcc aga cgc gct tca aat gaa ttc ttt atg tgt gga ggg cag tgt caa    1208
Ala Arg Arg Ala Ser Asn Glu Phe Phe Met Cys Gly Gly Gln Cys Gln
    375                 380                 385 cct act gtg tca cct cac agc gaa aca gcc cca att cca gtt cct act    1256
Pro Thr Val Ser Pro His Ser Glu Thr Ala Pro Ile Pro Val Pro Thr
390                 395                 400                 405 caa gta agg aat tat cag cgc ata gaa cag aat ctt ata tcc act gcc    1304
Gln Val Arg Asn Tyr Gln Arg Ile Glu Gln Asn Leu Ile Ser Thr Ala
                410                 415                 420 agc tct ggc aca aac cca cat ggt tct cca aga tct gca gta gta cga    1352
Ser Ser Gly Thr Asn Pro His Gly Ser Pro Arg Ser Ala Val Val Arg
            425                 430                 435 agg tct aat acc agc ccc atg ggc ttc ctc cgg gtt ggg tcc tgc tcc    1400
Arg Ser Asn Thr Ser Pro Met Gly Phe Leu Arg Val Gly Ser Cys Ser
        440                 445                 450 cct gta cca gga gac aca gtg cag aca gga gga cga aga ctc tct act    1448
Pro Val Pro Gly Asp Thr Val Gln Thr Gly Gly Arg Arg Leu Ser Thr
    455                 460                 465 ggc tct tcc agg cct tac tca cca tcc ccc ttg gtt ggt acc att cct    1496
Gly Ser Ser Arg Pro Tyr Ser Pro Ser Pro Leu Val Gly Thr Ile Pro
470                 475                 480                 485 gaa cag ttt agt cag tgc tgc tgt gga cat cct cag ggc cat gaa gcc    1544
Glu Gln Phe Ser Gln Cys Cys Cys Gly His Pro Gln Gly His Glu Ala
                490                 495                 500 agg agt agg cac tcc tca ggt tct cca gtg cca cag acc cag gca cca    1592
Arg Ser Arg His Ser Ser Gly Ser Pro Val Pro Gln Thr Gln Ala Pro
            505                 510                 515 cag tca ctc tta ctg ggt gct aga ctg cag agt gca ccc acc ctc acc    1640
Gln Ser Leu Leu Leu Gly Ala Arg Leu Gln Ser Ala Pro Thr Leu Thr
        520                 525                 530 gat atc tat cag aac aag cag aag ctc aga aag cag cac tct gac cct    1688
Asp Ile Tyr Gln Asn Lys Gln Lys Leu Arg Lys Gln His Ser Asp Pro
    535                 540                 545 gtg tgt ccg tcc cat gct gga gct ggg tat agt tac tca cct cag cct    1736
Val Cys Pro Ser His Ala Gly Ala Gly Tyr Ser Tyr Ser Pro Gln Pro
550                 555                 560                 565 agt cgg cct ggc agc ctt ggg acc tct ccc acc aag cac acg ggg tcc    1784
Ser Arg Pro Gly Ser Leu Gly Thr Ser Pro Thr Lys His Thr Gly Ser
                570                 575                 580 tct cca cgg aat tct gac tgg ttc ttt aaa act cct tta cca aca atc    1832
Ser Pro Arg Asn Ser Asp Trp Phe Phe Lys Thr Pro Leu Pro Thr Ile
            585                 590                 595 att ggc tct cct act aag act aca gct cct ttc aaa atc cct aaa aca    1880
Ile Gly Ser Pro Thr Lys Thr Thr Ala Pro Phe Lys Ile Pro Lys Thr
        600                 605                 610
```

-continued

| | |
|---|---|
| caa gca tct tct aac ctg tta gcc ttg gtt act cgt cat ggg cct gct<br>Gln Ala Ser Ser Asn Leu Leu Ala Leu Val Thr Arg His Gly Pro Ala<br>615                 620                 625 | 1928 |
| gaa agc cag tcc aaa gat ggg aat gac cct cgt gag tgt tcc cac tgc<br>Glu Ser Gln Ser Lys Asp Gly Asn Asp Pro Arg Glu Cys Ser His Cys<br>630                 635                 640                 645 | 1976 |
| ctc tca gta caa gga agc gag agg cat cga tct gag cag cag cag agc<br>Leu Ser Val Gln Gly Ser Glu Arg His Arg Ser Glu Gln Gln Gln Ser<br>             650                 655                 660 | 2024 |
| aag gca gtg ttt ggc aga tct gtc agt act ggg aag tta tca gaa caa<br>Lys Ala Val Phe Gly Arg Ser Val Ser Thr Gly Lys Leu Ser Glu Gln<br>                 665                 670                 675 | 2072 |
| caa gta aag gca cct tta ggt gga cac cag ggc agc acg gat agt tta<br>Gln Val Lys Ala Pro Leu Gly Gly His Gln Gly Ser Thr Asp Ser Leu<br>680                 685                 690 | 2120 |
| aac aca gaa cga cca atg gat gta gct cct gca gga gcc tgt ggt gtt<br>Asn Thr Glu Arg Pro Met Asp Val Ala Pro Ala Gly Ala Cys Gly Val<br>695                 700                 705 | 2168 |
| atg ctg gca ttg cca gca gga aca gca gca agc gcc aga gct gtc ctc<br>Met Leu Ala Leu Pro Ala Gly Thr Ala Ala Ser Ala Arg Ala Val Leu<br>710                 715                 720                 725 | 2216 |
| ttc acc gtg ggg tct cct cca cac agt gcc aca gcc ccc act tgt act<br>Phe Thr Val Gly Ser Pro Pro His Ser Ala Thr Ala Pro Thr Cys Thr<br>                 730                 735                 740 | 2264 |
| cat atg gtc ctt cga aca aga acc acc tca gtg ggg tcc agc agc tca<br>His Met Val Leu Arg Thr Arg Thr Thr Ser Val Gly Ser Ser Ser Ser<br>             745                 750                 755 | 2312 |
| gga ggt tcc ttg tgt tct gca agt ggc cga gta tgt gtg ggc tcc cct<br>Gly Gly Ser Leu Cys Ser Ala Ser Gly Arg Val Cys Val Gly Ser Pro<br>                 760                 765                 770 | 2360 |
| cct gga cca ggg ttg ggc tct tcc cca cca gga gca gag gga gct ccc<br>Pro Gly Pro Gly Leu Gly Ser Ser Pro Pro Gly Ala Glu Gly Ala Pro<br>775                 780                 785 | 2408 |
| agc cta aga tac gtg cct tat ggt gct tca cca ccc agc cta gag ggt<br>Ser Leu Arg Tyr Val Pro Tyr Gly Ala Ser Pro Pro Ser Leu Glu Gly<br>790                 795                 800                 805 | 2456 |
| ctc atc acc ttt gaa gcc cct gaa cta cca gag gag aca ctg atg gag<br>Leu Ile Thr Phe Glu Ala Pro Glu Leu Pro Glu Glu Thr Leu Met Glu<br>                 810                 815                 820 | 2504 |
| cga gag cac aca gac acc tta cgc cat ctg aac atg atg tta atg ttt<br>Arg Glu His Thr Asp Thr Leu Arg His Leu Asn Met Met Leu Met Phe<br>             825                 830                 835 | 2552 |
| act gag tgt gtg ctg gac ctg acg gca gtg agg ggt ggg aac cct gag<br>Thr Glu Cys Val Leu Asp Leu Thr Ala Val Arg Gly Gly Asn Pro Glu<br>                 840                 845                 850 | 2600 |
| ctg tgc aca tct gct gtg tcc ttg tac cag att cag gag agt gta gtt<br>Leu Cys Thr Ser Ala Val Ser Leu Tyr Gln Ile Gln Glu Ser Val Val<br>855                 860                 865 | 2648 |
| gtg gac cag atc agc cag cta agc aaa gat tgg ggg cgg gtg gag cag<br>Val Asp Gln Ile Ser Gln Leu Ser Lys Asp Trp Gly Arg Val Glu Gln<br>870                 875                 880                 885 | 2696 |
| ctg gtg ttg tac atg aag gca gca cag ctg ctg gcg gct tcc ctg cat<br>Leu Val Leu Tyr Met Lys Ala Ala Gln Leu Leu Ala Ala Ser Leu His<br>             890                 895                 900 | 2744 |
| ctc gcc aaa gct cag gtc aag tct ggg aag ctg agc cca tcc atg gct<br>Leu Ala Lys Ala Gln Val Lys Ser Gly Lys Leu Ser Pro Ser Met Ala<br>905                 910                 915 | 2792 |
| gtg aaa caa gtt gtt aaa aat ctg aat gaa aga tac aaa ttc tgc atc<br>Val Lys Gln Val Val Lys Asn Leu Asn Glu Arg Tyr Lys Phe Cys Ile<br>920                 925                 930 | 2840 |

```
acc atg tgc aag aaa ctt aca gaa aag ctg aat cgc ttc ttc tcc gat    2888
Thr Met Cys Lys Lys Leu Thr Glu Lys Leu Asn Arg Phe Phe Ser Asp
    935                 940                 945 aaa cag aga ttt att gat gaa atc aac agt gtg act gca gag aaa ctc    2936
Lys Gln Arg Phe Ile Asp Glu Ile Asn Ser Val Thr Ala Glu Lys Leu
950                 955                 960                 965 atc tat aat tgt gct gtg gaa atg gtt caa tct gca gcc ctg gat gag    2984
Ile Tyr Asn Cys Ala Val Glu Met Val Gln Ser Ala Ala Leu Asp Glu
            970                 975                 980 atg ttt cag cag act gaa gac atc gtt tat cgc tac cac aag gca gcc    3032
Met Phe Gln Gln Thr Glu Asp Ile Val Tyr Arg Tyr His Lys Ala Ala
        985                 990                 995 gtt ctt ttg gaa ggc tta agt aag atc ctg cag gac cct aca gat gtt    3080
Val Leu Leu Glu Gly Leu Ser Lys Ile Leu Gln Asp Pro Thr Asp Val
    1000                1005                1010 gaa aat gtg cat aag tat aaa tgt agt att gaa aga aga ttg tca gca    3128
Glu Asn Val His Lys Tyr Lys Cys Ser Ile Glu Arg Arg Leu Ser Ala
    1015                1020                1025 ctc tgc tgt agc act gca act gtg tgagtagcag gcttgtccgt ggactggcat   3182
Leu Cys Cys Ser Thr Ala Thr Val
1030                1035 ggaacaggag gtgatacatt tgggattacg tcttggttct gtcacccatc ccaggacagt  3242
gtggtgacta ccaaagaaca agcagcagct taagaaggaa gaacaataca aaaccactac  3302
atattgtaga aaacctgcct tattggagaa gtcactcccc cttttccttc tcttcataaa  3362
agcagaacaa aaagttttcc acatggctca agttatttga acctggcaaa taataaatgt  3422
accttagaac tagaaaaaaa aaaaaaaaaa aaa                               3455
```

<210> SEQ ID NO 21
<211> LENGTH: 1037
<212> TYPE: PRT
<213> ORGANISM: Mus musculus

<400> SEQUENCE: 21

```
Met Glu Val Val Gly Asp Phe Glu Tyr Cys Lys Arg Asp Leu Val Gly
1               5                   10                  15

His Gly Ala Phe Ala Val Val Phe Arg Gly Arg His Arg Gln Lys Thr
            20                  25                  30

Asp Trp Glu Val Ala Ile Lys Ser Ile Asn Lys Lys Asn Leu Ser Lys
        35                  40                  45

Ser Gln Ile Leu Leu Gly Lys Glu Ile Lys Ile Leu Lys Glu Leu Gln
    50                  55                  60

His Glu Asn Ile Val Ala Leu Tyr Asp Val Gln Glu Leu Pro Asn Ser
65                  70                  75                  80

Val Phe Leu Val Met Glu Tyr Cys Asn Gly Gly Asp Leu Ala Asp Tyr
                85                  90                  95

Leu Gln Ala Lys Gly Thr Leu Ser Glu Asp Thr Ile Arg Val Phe Leu
            100                 105                 110

His Gln Ile Ala Ala Ala Met Arg Ile Leu His Ser Lys Gly Ile Ile
        115                 120                 125

His Arg Asp Leu Lys Pro Gln Asn Ile Leu Leu Ser Tyr Ala Asn Arg
    130                 135                 140

Arg Lys Ser Asn Val Ser Gly Ile Arg Ile Lys Ile Ala Asp Phe Gly
145                 150                 155                 160

Phe Ala Arg Tyr Leu His Ser Asn Thr Met Ala Ala Thr Leu Cys Gly
                165                 170                 175
```

-continued

```
Ser Pro Met Tyr Met Ala Pro Glu Val Ile Met Ser Gln His Tyr Asp
            180                 185                 190
Ala Lys Ala Asp Leu Trp Ser Ile Gly Thr Val Ile Tyr Gln Cys Leu
        195                 200                 205
Val Gly Lys Pro Pro Phe Gln Ala Asn Ser Pro Gln Asp Leu Arg Met
    210                 215                 220
Phe Tyr Glu Lys Asn Arg Ser Leu Met Pro Ser Ile Pro Arg Glu Thr
225                 230                 235                 240
Ser Pro Tyr Leu Ala Asn Leu Leu Gly Leu Leu Gln Arg Asn Gln
                245                 250                 255
Lys Asp Arg Met Asp Phe Glu Ala Phe Phe Ser His Pro Phe Leu Glu
            260                 265                 270
Gln Val Pro Val Lys Lys Ser Cys Pro Val Pro Val Pro Val Tyr Ser
        275                 280                 285
Gly Pro Val Pro Gly Ser Cys Ser Ser Ser Pro Ser Cys Arg Phe
    290                 295                 300
Ala Ser Pro Pro Ser Leu Pro Asp Met Gln His Ile Gln Glu Glu Asn
305                 310                 315                 320
Leu Ser Ser Pro Pro Leu Gly Pro Pro Asn Tyr Leu Gln Val Ser Lys
                325                 330                 335
Asp Ser Ala Ser Asn Ser Ser Lys Asn Ser Ser Cys Asp Thr Asp Asp
            340                 345                 350
Phe Val Leu Val Pro His Asn Ile Ser Ser Asp His Ser Tyr Asp Met
            355                 360                 365
Pro Met Gly Thr Thr Ala Arg Arg Ala Ser Asn Glu Phe Phe Met Cys
        370                 375                 380
Gly Gly Gln Cys Gln Pro Thr Val Ser Pro His Ser Glu Thr Ala Pro
385                 390                 395                 400
Ile Pro Val Pro Thr Gln Val Arg Asn Tyr Gln Arg Ile Glu Gln Asn
                405                 410                 415
Leu Ile Ser Thr Ala Ser Ser Gly Thr Asn Pro His Gly Ser Pro Arg
            420                 425                 430
Ser Ala Val Val Arg Arg Ser Asn Thr Ser Pro Met Gly Phe Leu Arg
        435                 440                 445
Val Gly Ser Cys Ser Pro Val Pro Gly Asp Thr Val Gln Thr Gly Gly
    450                 455                 460
Arg Arg Leu Ser Thr Gly Ser Ser Arg Pro Tyr Ser Pro Ser Pro Leu
465                 470                 475                 480
Val Gly Thr Ile Pro Glu Gln Phe Ser Gln Cys Cys Cys Gly His Pro
                485                 490                 495
Gln Gly His Glu Ala Arg Ser Arg His Ser Ser Gly Ser Pro Val Pro
            500                 505                 510
Gln Thr Gln Ala Pro Gln Ser Leu Leu Leu Gly Ala Arg Leu Gln Ser
        515                 520                 525
Ala Pro Thr Leu Thr Asp Ile Tyr Gln Asn Lys Gln Lys Leu Arg Lys
    530                 535                 540
Gln His Ser Asp Pro Val Cys Pro Ser His Ala Gly Ala Gly Tyr Ser
545                 550                 555                 560
Tyr Ser Pro Gln Pro Ser Arg Pro Gly Ser Leu Gly Thr Ser Pro Thr
                565                 570                 575
Lys His Thr Gly Ser Ser Pro Arg Asn Ser Asp Trp Phe Phe Lys Thr
            580                 585                 590
```

-continued

```
Pro Leu Pro Thr Ile Ile Gly Ser Pro Thr Lys Thr Thr Ala Pro Phe
        595                 600                 605

Lys Ile Pro Lys Thr Gln Ala Ser Ser Asn Leu Leu Ala Leu Val Thr
        610                 615                 620

Arg His Gly Pro Ala Glu Ser Gln Ser Lys Asp Gly Asn Asp Pro Arg
625                 630                 635                 640

Glu Cys Ser His Cys Leu Ser Val Gln Gly Ser Glu Arg His Arg Ser
                645                 650                 655

Glu Gln Gln Gln Ser Lys Ala Val Phe Gly Arg Ser Val Ser Thr Gly
                660                 665                 670

Lys Leu Ser Glu Gln Gln Val Lys Ala Pro Leu Gly Gly His Gln Gly
        675                 680                 685

Ser Thr Asp Ser Leu Asn Thr Glu Arg Pro Met Asp Val Ala Pro Ala
        690                 695                 700

Gly Ala Cys Gly Val Met Leu Ala Leu Pro Ala Gly Thr Ala Ala Ser
705                 710                 715                 720

Ala Arg Ala Val Leu Phe Thr Val Gly Ser Pro Pro His Ser Ala Thr
                725                 730                 735

Ala Pro Thr Cys Thr His Met Val Leu Arg Thr Arg Thr Thr Ser Val
                740                 745                 750

Gly Ser Ser Ser Gly Gly Ser Leu Cys Ser Ala Ser Gly Arg Val
        755                 760                 765

Cys Val Gly Ser Pro Pro Gly Pro Gly Leu Gly Ser Ser Pro Pro Gly
770                 775                 780

Ala Glu Gly Ala Pro Ser Leu Arg Tyr Val Pro Tyr Gly Ala Ser Pro
785                 790                 795                 800

Pro Ser Leu Glu Gly Leu Ile Thr Phe Glu Ala Pro Glu Leu Pro Glu
                805                 810                 815

Glu Thr Leu Met Glu Arg Glu His Thr Asp Thr Leu Arg His Leu Asn
                820                 825                 830

Met Met Leu Met Phe Thr Glu Cys Val Leu Asp Leu Thr Ala Val Arg
                835                 840                 845

Gly Gly Asn Pro Glu Leu Cys Thr Ser Ala Val Ser Leu Tyr Gln Ile
        850                 855                 860

Gln Glu Ser Val Val Asp Gln Ile Ser Gln Leu Ser Lys Asp Trp
865                 870                 875                 880

Gly Arg Val Glu Gln Leu Val Leu Tyr Met Lys Ala Ala Gln Leu Leu
                885                 890                 895

Ala Ala Ser Leu His Leu Ala Lys Ala Gln Val Lys Ser Gly Lys Leu
        900                 905                 910

Ser Pro Ser Met Ala Val Lys Gln Val Val Lys Asn Leu Asn Glu Arg
        915                 920                 925

Tyr Lys Phe Cys Ile Thr Met Cys Lys Lys Leu Thr Glu Lys Leu Asn
        930                 935                 940

Arg Phe Phe Ser Asp Lys Gln Arg Phe Ile Asp Glu Ile Asn Ser Val
945                 950                 955                 960

Thr Ala Glu Lys Leu Ile Tyr Asn Cys Ala Val Glu Met Val Gln Ser
                965                 970                 975

Ala Ala Leu Asp Glu Met Phe Gln Gln Thr Glu Asp Ile Val Tyr Arg
                980                 985                 990

Tyr His Lys Ala Ala Val Leu Leu Glu Gly Leu Ser Lys Ile Leu Gln
        995                 1000                1005
```

```
Asp Pro Thr Asp Val Glu Asn Val His Lys Tyr Lys Cys Ser Ile Glu
    1010             1015                 1020

Arg Arg Leu Ser Ala Leu Cys Cys Ser Thr Ala Thr Val
1025             1030             1035
```

SERINE/THEONINE PROTEIN KINASE

This application is a continuation-in-part of PCT/JP98/01246, filed Mar. 23, 1998, and claims priority from Japanese Application No. 9/124798, filed Apr. 28, 1997.

TECHNICAL FIELD

The present invention relates to a useful serine/threonine protein kinase, a DNA encoding the protein kinase, a vector comprising the DNA, a host harboring the vector, and an antibody that binds to the protein kinase.

BACKGROUND ART

Protein kinase is an enzyme that phosphorylates serine, threonine, or tyrosine residues of substrate proteins, and numerous protein kinase families are known. It is known that protein kinase controls various biological phenomena by regulating the intracellular signal transduction system through protein phosphorylation (Hunter, T., A thousand and one protein kinases, Cell, 50:823–829, 1987).

One of a group of nematode (C. elegans) mutants (uncoordinated), "unc-51," causes movement disorder and a responsible gene "UNC-51" found in unc-51 reportedly encodes a novel serine/threonine protein kinase (Ogura, K. et al., Caenorhabditis elegans unc-51 gene required for axonal elongation encodes a novel serine/threonine kinase, Genes Dev., 8:2389–2400, 1994). The result of tissue staining confirmed that the unc-51 mutant has axonal elongation disorder, and the UNC-51 kinase gene was thought to be essential for axonal elongation (Ogura, K. et al., Caenorhabditis elegans unc-51 gene required for axonal elongation encodes a novel serine/threonine kinase, Genes Dev., 8:2389–2400, 1994).

The mechanism of axonal biosynthesis in mammals has not been revealed yet at the molecular level. C. elegans is an excellent experimental model for axonal biosynthesis, and the involvement of similar molecules in both mammals and C. elegans has been suggested. The isolation of mammalian molecule having the similar function as the UNC-51 kinase of the nematode has been desired.

DISCLOSURE OF THE INVENTION

An objective of the present invention is to provide a mammalian serine/threonine protein kinase involved in axonal formation.

As a result of research to achieve the above objective, the inventors successfully isolated a mouse cDNA encoding a protein comprising a serine/threonine protein kinase region by effecting PCR using a synthetic DNA corresponding to the kinase-conserved region as a primer and a rat cDNA as a template, and screening a mouse cDNA library using the DNA fragment thus obtained as a probe. The multiple human and mouse cDNAs having the similar structure to the isolated mouse cDNA were successfully isolated based on the sequence of the isolated mouse cDNA. The inventors synthesized an antisense DNA against the isolated mouse cDNA, and its effect on a nerve cell was studied to confirm that the antisense DNA inhibits axonal elongation.

The present invention relates to a mammalian serine/threonine protein kinase involved in axonal formation. More specifically, the invention relates to:

(1) a protein comprising the amino acid sequence set forth in SEQ ID NO: 2, 4, 14, 16, or 21, or a protein comprising the amino acid sequence set forth in SEQ ID NO: 2, 4, 14, 16, or 21, in which one or more amino acids are substituted, deleted, or added, wherein said protein has activity of serine/threonine protein kinase;

(2) a protein encoded by a DNA hybridizing with a DNA comprising the nucleotide sequence set forth in SEQ ID NO: 1, 3, 13, 15, or 20, wherein said protein has the activity of serine/threonine protein kinase;

(3) a protein comprising the amino acid sequence set forth in SEQ ID NO: 2, 4, 14, 16, or 21, or a protein comprising the amino acid sequence set forth in SEQ ID NO: 2, 4, 14, 16, or 21, in which one or more amino acids are substituted, deleted, or added, wherein said protein induces axonal elongation;

(4) a protein encoded by a DNA hybridizing with a DNA comprising the nucleotide sequence set forth in SEQ ID NO: 1, 3, 13, 15, or 20, wherein said protein induces axonal elongation;

(5) the protein of (2) or (4), wherein said protein is derived from a mammal;

(6) a DNA encoding any one of the proteins of (1) to (5);

(7) an antisense DNA against a DNA comprising the nucleotide sequence set forth in SEQ ID NO: 1, 3, 13, 15, or 20 or a part thereof, wherein said DNA or a part thereof-inhibits axonal elongation;

(8) a vector comprising the DNA of (6) or (7);

(9) a host cell harboring the vector of (8); and

(10) an antibody that binds to the protein of (1) or (2).

A "protein" used herein includes a peptide with a short amino acid sequence.

The present invention relates to a mammal-derived serine/threonine protein kinase involved in axonal formation. The inventors isolated a mouse cDNA highly homologous to the kinase region of UNC-51, a serine/threonine kinase that induces axonal elongation in a nematode, C. elegans (Ogura, K. et al., Caenorhabditis elegans unc-51 gene required for axonal elongation encodes a novel serine/threonine kinase, Genes Dev., 8:2389–2400, 1994) (this clone was named "MUK1"). The nucleotide sequence of the MUK1 cDNA is shown in SEQ ID NO: 1. The inventors also isolated four cDNAs comprising the similar structure to the MUK1 cDNA by screening a human cerebellum library, a mouse cerebellum library, a human NH-2 cell library, and a mouse brain library, based on the sequence of MUK1. The isolated four cDNAs were considered to be a human counterpart (SEQ ID NO: 3), a splicing valiant (SEQ ID NO: 13), a human homologue (SEQ ID NO: 15), and a family gene (SEQ ID NO: 20) (named "MUK2") of MUK1 considering their structural characteristics. The analysis of structures of the proteins encoded by these isolated cDNAs confirmed that all the proteins possess the kinase-conserved region. This fact indicates that those proteins would be involved in signal transduction through phosphorylation of other proteins. When an antisense DNA against the MUK1 cDNA (SEQ ID NO: 8) was added to Neuro2A cells derived from neuroblast cells, axonal elongation in the cells was inhibited. Those proteins may thus be involved in axonal elongation by signal transduction through phosphorylation of other proteins.

Among these proteins, the protein (SEQ ID NO: 4) encoded by cDNA set forth in SEQ ID NO: 3 is a partial sequence comprising the sequence corresponding to the serine/threonine protein kinase region. A protein encoded by the full-length DNA can be obtained by methods well known in the art. For example, the full-length DNA is isolated by screening a library with a partial sequence of the DNA of SEQ ID NO: 3 as probe or by PCR (Current protocols in Molecular Biology ed. by Ausubel et al. (1987) published by John Wiley & Sons, Section 6.1–6.4), the isolated full-length DNA is introduced into cultured cells such as COS cells to express the protein in the cells (Current Protocols in Molecular Biology, ed. by Ausubel et al. (1987) published by John Wiley & Sons, Section 9.1–9.9), then the protein is purified. The thus-isolated protein is also included in the protein of this invention.

Functional equivalents to the protein set forth in SEQ ID NO: 2, 4, 14, 16, or 21 can be obtained by substituting amino acid residue(s) of these proteins using usually used methods such as site-directed mutagenesis (Current Protocols in Molecular Biology, ed. by Ausubel et al. (1987) published by John Wiley & Sons, Section 8.1–8.5). This invention also includes proteins functionally equivalent to the protein of SEQ ID NO: 2, 4, 14, 16, or 21, in which one or more amino acids are substituted, deleted, or added. Alternatively, functionally equivalent proteins to the protein of SEQ ID NO: 2, 4, 14, 16, or 21 can be obtained by isolating DNAs highly homologous to DNA sequences (or a part thereof) of SEQ ID NO: 1, 3, 13, 15, and 20, using the known hybridization technique (Current Protocols in Molecular Biology, ed. by Ausubel et al. (1987) published by John Wiley & Sons, Sections 6.3, 6.4). The protein of the present invention includes such proteins functionally equivalent to the proteins of SEQ ID NO: 2, 4, 14, 16, and 21, encoded by a DNA hybridizing with the DNA of SEQ ID NO: 1, 3, 13, 15, or 20. The functionally equivalent proteins obtained by the hybridization technique are highly homologous in the amino acid sequence to the protein of SEQ ID NO: 2, 4, 14, 16, or 21 in general. High homology is preferably 60% or more, more preferably 80% or more, and most preferably 95% or more. The hybridization and washing conditions for isolating DNA encoding a functionally equivalent protein are defined as low stringency: 37° C., 1×SSC, 0.1% SDS; moderate stringency: 42° C., 0.5×SSC, 0.1% SDS; and high stringency: 65° C., 0.2×SSC, 0.1% SDS. The "DNA hybridizing with" used herein include not only full-length DNAs hybridizing with the DNA of SEQ ID NO: 1, 3, 13, 15, or 20, but also DNAs comprising a region hybridizing with the above DNA. A "functionally equivalent protein" means a protein that having the serine/threonine protein kinase activity similar to that of the protein of SEQ ID NO: 2, 4, 14, 16, or 21, and/or induces axonal elongation. "Serine/threonine protein kinase activity" means biochemical activity to phosphorylate substrate proteins and cellular biological activity induced by this biochemical activity. The biochemical activity of the serine/threonine protein kinase can be detected as autophosphorylation—and phosphorylation of basic proteins (such as a myelin basic protein, histone, or tau protein) in the presence of magnesium ions and ATP (Protein Kinase and Phosphatase, D. G. Hardie, translated by H. Hidaka, Medical Science International, p101–120). On the other hand, the biological activity can be detected as the cellular change when a DNA encoding serine/threonine protein kinase or its variant is expressed in cells (Muramatsu, M. et al., Protein Kinase and Signal Transduction: Studies with mutant protein kinases (1993) p185–192, The mechanism and new approach on drug resistance of cancer cells, The Elsevier Science Publishers). The "axonal elongation-inducing activity" can be detected by, for example, by introducing a DNA encoding the protein of the invention into cultured nerve cells such as Nero2A cells, PC12 cells, and NT-2 cells (Stratagene) and observing the cells under a phase-contrast microscope (Ulloa, et al., Depletion of casein kinase II by antisense oligonucleotide prevents neuritogenesis in neuroblastoma cells, EMBO. J., 12:1633–1640, 1993).

The protein of the present invention can be prepared as a recombinant protein or a natural protein. A recombinant protein can be prepared, for example, by inserting a DNA encoding the protein of the invention (e.g., the DNA of SEQ ID NO: 1, 3, 13, 15, or 20) into an appropriate expression vector, introducing the vector into a host cell, expressing the protein in the transformant, and purifying the protein, as described later. A natural protein can be prepared by the standard methods, for example, using an affinity column with an antibody (Current Protocols in Molecular Biology ed. by Ausubel et al. (1987) published by John and Wiley & Sons, Section 16.1–16.19). The antibody can be either a monoclonal antibody or a polyclonal antibody. A polyclonal antibody can be obtained by synthesizing oligopeptides corresponding to the amino acid sequence of interest and immunizing a rabbit with it, following the standard method (Current Protocols in Molecular Biology ed. by Ausubel et al. (1987) published by John Wiley & Sons, Section 11.12–11.13). A monoclonal antibody can be prepared by immunizing a mouse with a purified protein of interest expressed in E. coli by a standard method, fusing a spleen cell and a myeloma cell to produce hybridoma cells, and then obtaining a monoclonal antibody from the hybridoma (Current Protocols in Molecular Biology ed. by Ausubel et al. (1987) published by John Wiley & Sons, Section 11.4–11.11). When an antibody that binds to the protein of the invention is used for antibody therapy, a human antibody or a humanized antibody that has low immunogenicity is preferably used. A human antibody can be prepared, for example, by immunizing a mouse whose immune system is replaced by the human system in the same manner as described above for producing the monoclonal antibody. A humanized antibody can be prepared by the recombinant DNA technology using hypervariable region of the monoclonal antibody (Methods in Enzymology, 203:99–121, 1991).

This invention also relates to the DNA encoding the above-described protein of the invention. The form of the DNA of the invention is not particularly limited as long as it encodes the protein of the invention, including cDNA, genomic DNA, chemically synthesized DNA, etc. The DNA of the present invention can be isolated by the standard method, such as the hybridization method using the DNA sequence of SEQ ID NO: 1, 3, 13, 15, or 20 as a probe, or PCR using the primers synthesized based on these DNA sequences. The DNA of the invention can be used to prepare recombinant proteins. That is, the protein of the invention can be prepared as a recombinant protein by inserting the DNA of this invention in an appropriate vector, introducing the vector into a host cell, and culturing the transformant. Any vector capable of stably maintaining the inserted DNA can be used without limitation. For example, Bluescript vector (Stratagene) is preferable when a host cell is E. coli. When a vector is used to produce the protein of the invention, an expression vector is especially useful. Any expression vector can be used without limitation as long as it expresses the protein of this invention in vitro, in E. coli, in a cultured cell line, or in vivo. For example, pBEST vector (Promega) is preferably used for expression in vitro, and pET vector (Invitrogen) for E. coli, pME18S vector (Mol Cell Biol. 8:466–472, 1988) for cultured cell lines and in vivo. The DNA of the invention can be inserted into a vector by the methods well known in the art, for example, ligation at the restriction enzyme site (Current Protocols in Molecular Biology ed. by Ausubel et al. (1987) published by John Wiley & Sons, Section 11. 4–11.11). A vector can be introduced into any host cell without limitation. For example, a cell capable of overexpressing the protein, such as COS cells and CHO cells, can be used. A vector can be introduced into a host cell by the method well known in the art, such as calcium phosphate precipitation, electroporation (Current Protocols in Molecular Biology ed. by Ausubel et al. (1987) published by John Wiley & Sons, Section 9.1–9.9), the lipofectamine method (GIBCO-BRL), or microinjection.

The DNA and its antisense DNA of the present invention can be used for promoting or inhibiting axonal elongation. Therefore, those DNAs are useful for diagnosis and gene therapy of various inherited neuropathy, senile dementia, Alzheimer's disease, and psychoneurosis, which cause axonal elongation disorder. For gene therapy, the above DNA or antisense DNA is inserted into a retrovirus vector or an adenovirus vector- and administered to a patient by the in vivo or ex vivo method. The antisense DNA can be prepared, for example, by the phosphorothioate method (Stein, 1988 Physicochemical properties of phosphorothioate oligodeoxynucleotides, Nucleic Acids Res. 16:3209–3221, 1988) based on the DNA sequence information of the invention (for example, the DNA of SEQ ID NO: 1, 3, 13, 15, or 20). The axonal elongation-inhibitory activity of the thus-prepared antisense DNA can be detected by observing cultured nerve cells such as Nero2A cells, PC12 cells, and NT-2 cells (Stratagene), into which the antisense DNA was introduced, under a phase-contrast microscope (Ulloa et al., Depletion of casein kinase II by antisense oligonucleotide prevents neuritogenesis in neuroblastoma cells, EMBO. J., 12:1633–1640, 1993).

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones: e.g., as these occur in a DNA library such as a cDNA or genomic DNA library.

The term "substantially pure" as used herein in reference to a given polypeptide means that the polypeptide is substantially free from other biological compounds, such as those in cellular material, viral material, or culture medium, with which the polypeptide was associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A "conservative amino acid substitution" is one in which an amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score=100, wordlength=12 to obtain nucleotide sequences homologous to a nucleic acid molecules of the invention. BLAST protein searches are performed with the XBLAST program, score= 50, wordlength=3 to obtain amino acid sequences homologous to a reference polypeptide. To obtain gapped alignments for comparison purposes, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

By "inhibiting" is meant any measurable level of inhibition, including, for example, 100% or 10% inhibition.

Unless otherwise defined, all technical and scientific terms used herein have the same meaning as commonly understood by one of ordinary skill in the art to which this invention belongs. In case of conflict, the present application, including definitions, will control. All publications, patent applications, patents, and other references mentioned herein are incorporated by reference. The materials, methods, and examples are illustrative only and not intended to be limiting. Other features and advantages of the invention will be apparent from the detailed description, and from the claims.

BRIEF DESCRIPTION OF THE DRAWINGS

FIG. 2A is the control without MUK1. FIG. 2B shows the effect of the MUK1 antisense DNA.

FIG. 3 compares the amino acid sequence of MUK1 and that of MUK2. The amino acid positions from 1 to 550 are shown.

FIG. 4 compares the amino acid sequence of MUK1 and that of MUK2. The amino acid positions from 551 to 1100 are shown.

DETAILED DESCRIPTION

Figure 1:
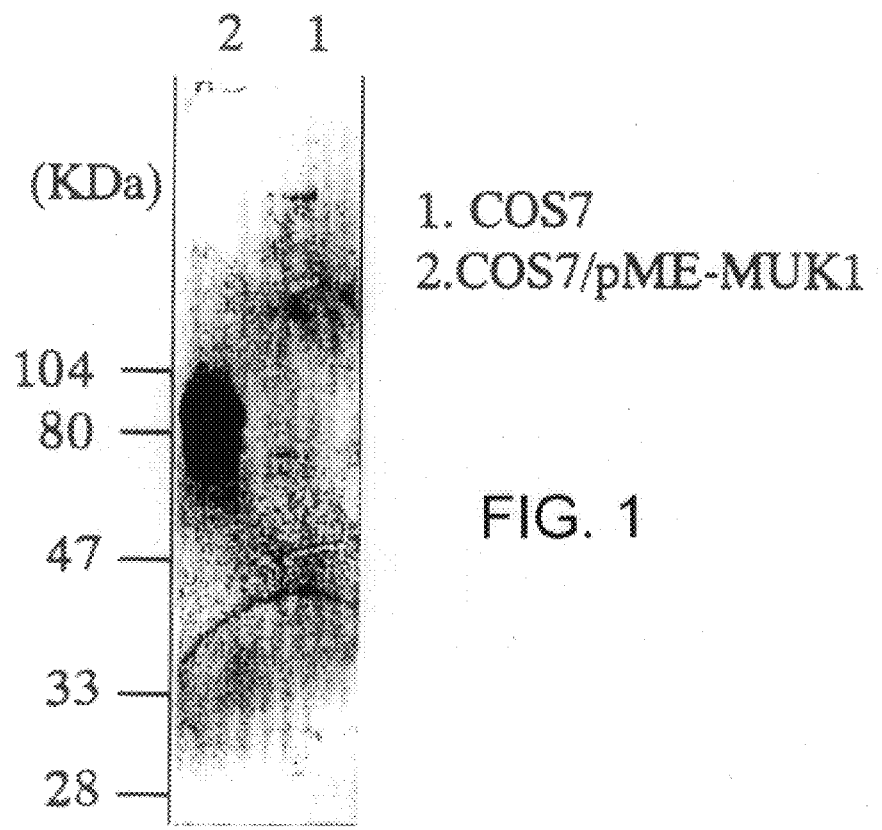
FIG. 1 is a fluorescent film image showing the MUK1 protein detected by immunoblotting. Lane 1 detects the control using the protein extracted from COS cells without the MUK1 protein expression vector, "pME-MUK1." Lane 2 detects the protein extracted from COS cells carrying pME-MUK1.

The present invention is illustrated in detail below with reference to examples, but is not to be construed as being limited thereto.

EXAMPLE 1
Screening a Mouse Serine/threonine Protein Kinase Gene

In order to obtain a novel serine/threonine protein kinase, PCR was conducted using synthetic DNA comprising the codons corresponding to the kinase-conserved region VIb (Ile-Ser-His-Arg-Glu-Leu-Gln) (SEQ ID NO: 5) and the kinase-conserved region VIII (Arg-Tyr-Met-Ala-Pro-Glu) (SEQ ID NO: 6) as the primers, and the single-stranded cDNA prepared by oligo-dT primers from rat fetal brain mRNA as a template. The fragment of 114 bp (SEQ ID NO: 9) was obtained. Subsequently, a mouse cerebellum library (Clontech) was screened using the fragment obtained above, and cDNA of 2673 bp (SEQ ID NO: 1) was isolated. The amino acid sequence deduced from the obtained cDNA showed 60% homology to the kinase region of serine/threonine kinase UNC-51 of a nematode, *C. elegans* (Ogura, K. et al., *Caenorhabditis elegans* unc-51 gene required for axonal elongation encodes a novel serine/threonine kinase, Genes Dev., 8:2389–2400, 1994). Homology in regions except the kinase region is low in general. However, four highly homologous regions comprising motif-like continuous 7 to 10 amino acids were found.

UNC-51 is a serine/threonine protein kinase identified in a nematode "*C. elegans*," mutant suffering from movement disorders. The mutant has axonal elongation disorder, which was confirmed by tissue staining (Hedgecock, E. M. et al., Axonal guidance of mutants of *C. elegans* identified by filling sensory neurons with fluorescein dyes, Dev. Biol. 111:158–170, 1985). Mutation was identified on the coding region of UNC-51 in multiple unc-51 mutants examined, and UNC-51 in which mutation was introduced into the ATP binding site of the kinase region causes dominant negative mutation.—Therefore, the function of UNC-51 as a protein kinase is considered to be essential for axonal formation (Ogura, K et al., *Caenorhabditis elegans* unc-51 gene required for axonal elongation encodes a novel serine/threonine kinase, Genes Dev., 8:2389–2400, 1994). The inventors named the obtained clone "Mammalian homologue of Unc-51 Kinase-1" (abbreviated as MUK1).

EXAMPLE 2
Screening Human MUK1 cDNA

MUK1 cDNA (SEQ ID NO: 1) was labeled with $^{32}$P using "Megaprime kit" (Amersham) to serve as a probe—for screening a human cerebellum cDNA (Clontech). $10^6$ clones from the library were transferred onto a nylon membrane (Amersham) and fixed by UV. The $^{32}$P-labeled probe was hybridized with the clones on the membrane in QuikHyb solution (Stratagene) overnight. The membrane was washed twice in 2×SSC and 0.1% SDS at room temperature for 20 min once in 0.2×SSC and 0.1% SDS at 65° C. for 10 min to detect positive clones using Kodak XO-mat (primary screening). The positive clones were subjected to the secondary and tertiary screenings using the same method as above. Consequently, a human cDNA hybridizing with the probe was obtained (SEQ ID NO: 3). The amino acid sequence deduced from the obtained human cDNA (SEQ ID NO: 4) showed 90% or more homology to MUK1.

EXAMPLE 3
Preparing an Antibody Against the MUK1 Protein and Determining the Molecular Weight of the MUK1 Protein The MUK1 cDNA of SEQ ID NO: 1 was inserted into the EcoRI site of pME18S expression vector (Mol. Cell Biol. 8:466–472, 1988) to prepare plasmid pME-MUK1. PME-MUK1 was introduced into COS cells using lipofectamine (BRL) to—temporarily express the cDNA. After 48 hours, the cells were lysed in a buffer solution (Tris-HCl (pH 7.5), 50 mM KCl, 5 mM EDTA) containing 0.2% Triton X-100. The solubilized protein was subjected to—SDS-PAGE (10% polyacrylamide) and transferred onto PVDF membrane (Immobilon) for immunoblotting. Polyclonal antibodies obtained by immunizing a rabbit with a peptide (SEQ ID NO: 10) corresponding to a part of the amino acid sequence derived from the MUK1 translation region were used as the primary antibody. Anti-rabbit Ig antibody (Amersham) was used as the secondary antibody. ECL kit (Amersham) was used for the detection. The band of the protein was obtained at about the molecular weight of 80 kD (FIG. 1).

EXAMPLE 4
Analyzing the MUK1 Function in Nerve Cells

In order to determine whether MUK1 elongates axon or not, the antisense DNA (SEQ ID NO: 11) was synthesized based on the nucleotide sequence of SEQ ID NO: 1 by the phosphorothioate (S-oligo) method. Similarly, the sense DNA (SEQ ID NO: 12) was synthesized.

Figure 2A:
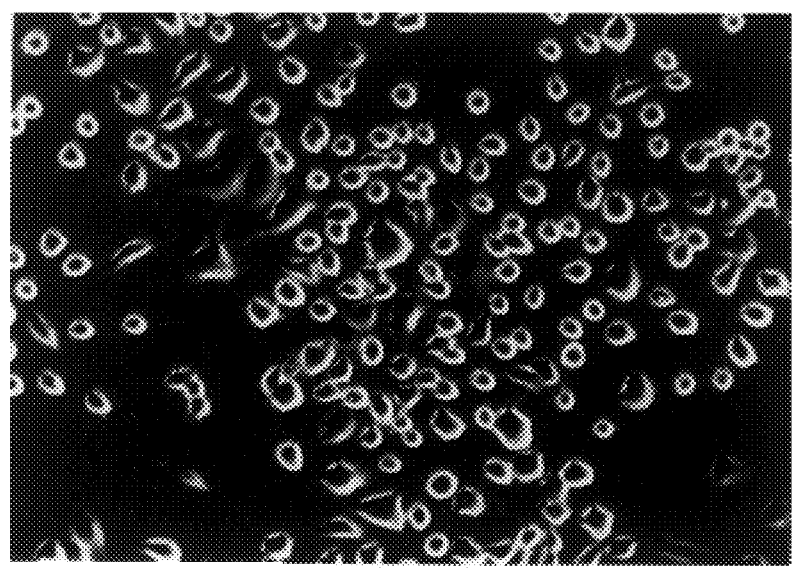
FIGS. 2A and 2B are micrographs detecting effects of MUK1 on axonal elongation.
Figure 2B:
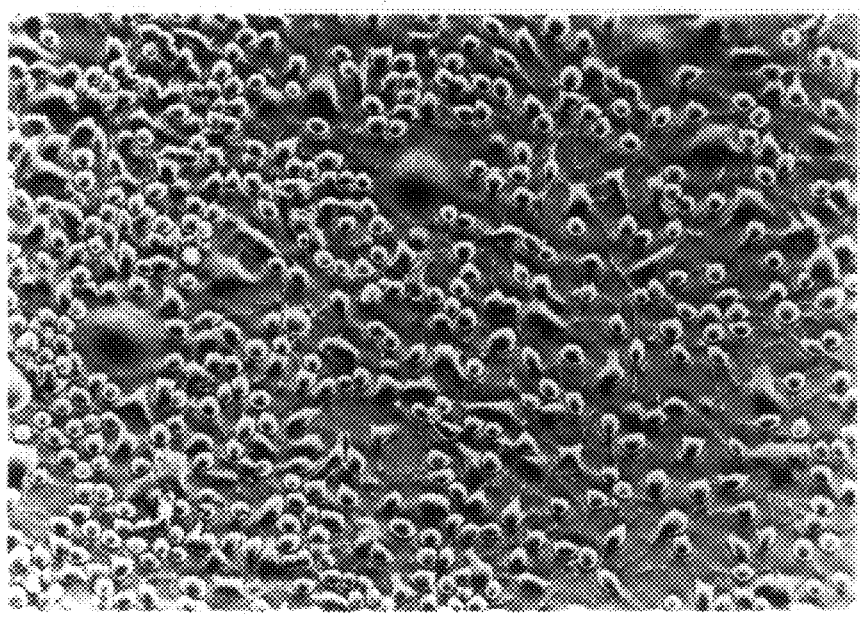
Figure 2C:
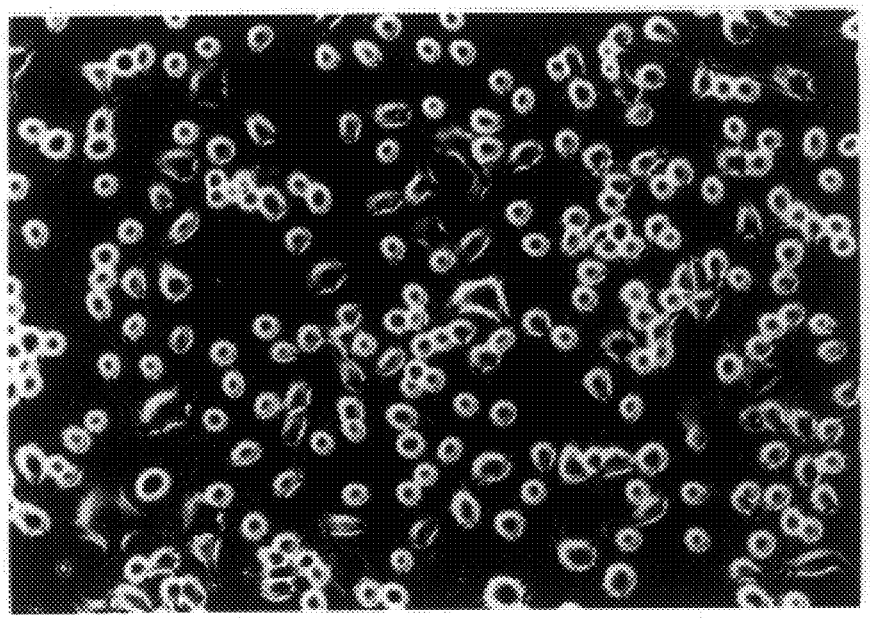
FIG. 2C shows the effect of the MUK1 sense DNA.

Neuro2A cells derived from neuroblastoma cells were transferred into ITS medium containing DMEM medium (Nikken Biology Medicine Laboratory), 5 mg/ml insulin, 5 mg/ml transferrin, and 5 ng/ml selenic acid to confirm that axon elongated. The antisense DNA (SEQ ID NO: 11) was then added to the ITS medium to determine whether axonal elongation of Neuro2A cells was inhibited or not. The addition of 10 µM antisense DNA (SEQ ID NO: 11) significantly inhibited axonal elongation (FIG. 2B), compared to the control (FIG. 2A). In contrast, axonal elongation was not inhibited when the same concentration of the sense DNA (SEQ ID NO: 12) was added (FIG. 2C).

EXAMPLE 5
Screening a Mouse Cerebellum Library Using the MUK1 cDNA as a Probe The MUK1 cDNA (SEQ ID NO: 1) was labeled with $^{32}$P by Megaprime kit (Amersham) to screen a mouse cerebellum library (Clontech). $10^6$ clones from the library were transferred onto a nylon membrane (Amersham) and fixed by UV. The $^{32}$P-labeled probe was hybridized with the clones on the membrane in QuikHyb solution (Stratagene) overnight. The membrane was washed twice in 2×SSC and 0.1% SDS at room temperature for 20 min and once in 0.2×SSC and 0.1% SDS at 65° C. for 10 min to detect positive clones using Kodak XO-mat (primary screening). The positive clones were subjected to the secondary and tertiary screenings using the same method as above. Consequently, a 3995 bp DNA fragment (SEQ ID NO: 13) was cloned. The amino acid sequence (SEQ ID NO: 14) deduced from ORF of SEQ ID NO: 13 has 575 N-terminal amino acids that are the same as the MUK1 protein (SEQ ID NO: 2), but the different carboxyl-terminal amino acids. This DNA fragment was thus considered to encode the splicing variant of MUK1.

EXAMPLE 6
Screening a Human NT-2 Cell Library Using the MUK1 cDNA as a Probe The MUK1 cDNA (SEQ ID NO: 1) was labeled with $^{32}$P using Megaprime Kit (Amersham) to screen a human NT-2 cell library. $10^6$ clones from the library were transferred onto a nylon membrane (Amersham) and fixed by UV. The 32P-labeled probe was hybridized with the clones on the membrane in QuikHyb solution (Stratagene) overnight. The membrane was washed twice in 2×SSC and 0.1% SDS at room temperature for 20 min and once in 0.2×SSC and 0.1% SDS at 65° C. for 10 min to detect positive clones using Kodak XO-mat (primary screening). The positive clones were subjected to the secondary and tertiary screenings using the same method as above. Consequently, a 5228 bp DNA fragment (SEQ ID NO: 15) was cloned. The amino acid sequence (SEQ ID NO: 16) deduced from ORF of this DNA fragment is 91% identical to the splicing variant of MUK1 (SEQ ID NO: 14).

EXAMPLE 7

Searching GenBank based on the deduced amino acid sequence of the MUK1 protein (SEQ ID NO: 2) found similar expressed sequence tag (EST) (GenBank Accession No. W29537). A DNA was synthesized based on this information (SEQ ID NO: 17 and SEQ ID NO: 18), and PCR was performed using the synthetic DNA and using a mouse brain cDNA library (GIBCO-BRL) as a template to obtain a 445 bp DNA fragment (SEQ ID NO: 19). This DNA fragment was $^{32}$P labeled with Megaprime kit (Amersham) and used to screen a mouse brain library (GIBCO-BRL). $10^6$ clones from the library were transferred onto a nylon membrane (Amersham) and fixed by UV. The $^{32}$P-labeled probe was hybridized with the clones on the membrane in QuikHyb solution (Stratagene) overnight. The membrane was washed twice in 2×SSC and 0.1% SDS at room temperature for 20 min and once in 0.2×SSC and 0.1% SDS at 65° C. for 10 min once to detect positive clones using Kodak XO-mat (primary screening). The positive clones were subjected to the secondary and tertiary screenings using the same method as above. Consequently, a 3455 bp DNA fragment (SEQ ID NO: 20) was successfully cloned. This clone was named MUK2.

The amino acid sequence (SEQ ID NO: 21) deduced from ORF of this DNA fragment is 82% identical to the kinase region of the MUK1 protein, and 44% to its control region, indicating that this clone is a family gene (FIGS. 3 and 4).

INDUSTRIAL APPLICABILITY

The present invention provides a serine/threonine protein kinase that is industrially highly useful. The serine/threonine protein kinase of this invention is involved in axonal elongation of mammals. Therefore, the serine/threonine protein kinase or its gene of the invention is useful for diagnosis and treatment of various inherited neuropathy, senile dementia, Alzheimer's disease, and psychoneurosis, which cause axonal elongation disorder. Low molecular weight molecules controlling kinase activity and biological activity of the serine/threonine protein kinase of the invention can be screened by assaying these activities

What is claimed is:

1. An isolated nucleic acid encoding a polypeptide comprising an amino acid sequence at least 80% identical to any one of SEQ ID NOs:2, 4, 14, 16, or 21, wherein the polypeptide phosphorylates a serine or threonine residue within a protein.

2. An isolated nucleic acid encoding a polypeptide comprising the amino acid sequence of any one of SEQ ID NOs:2, 4, 14, 16, or 21.

3. An isolated nucleic acid encoding a polypeptide consisting of the amino acid sequence of any one of SEQ ID NOs:2, 4, 14, 16, or 21.

4. An isolated nucleic acid which encodes a polypeptide that phosphorylates a serine or threonine residue within a protein and hybridizes under high stringency conditions to a nucleic acid molecule consisting of any one of SEQ ID NOs: 1, 3, 13, 15, or 20, or the complement of any one of SEQ ID NOs:1, 3, 13, 15, or 20, wherein said high stringency conditions comprise hybridizing in 0.2×SSC and 0.1% SDS at 65° C. and washing in 0.2×SSC and 0.1% SDS at 65° C.

5. The isolated nucleic acid of claim 1, wherein the nucleic acid encodes a polypeptide comprising an amino acid sequence at least 90% identical to any one of SEQ ID NOs:2, 4, 14, 16, or 21, wherein the polypeptide phosphorylates a serine or threonine residue within a protein.

6. The isolated nucleic acid of claim 1, wherein the nucleic acid encodes a polypeptide comprising an amino acid sequence at least 95% identical to any one of SEQ ID NOs:2, 4, 14, 16, or 21, wherein the polypeptide phosphorylates a serine or threonine residue within a protein.

7. A vector comprising the nucleic acid of claim 1.
8. A vector comprising the nucleic acid of claim 2.
9. A vector comprising the nucleic acid of claim 3.
10. A vector comprising the nucleic acid of claim 4.
11. A vector comprising the nucleic acid of claim 5.
12. A cultural host cell comprising the nucleic acid of claim 1.
13. A cultural host cell comprising the nucleic acid of claim 2.
14. A cultural host cell comprising the nucleic acid of claim 3.
15. A cultural host cell comprising the nucleic acid of claim 4.
16. A cultural host cell comprising the nucleic acid of claim 5.
17. A vector comprising the nucleic acid of claim 6.
18. A cultured host cell comprising the nucleic acid of claim 6.

* * * * *

UNITED STATES PATENT AND TRADEMARK OFFICE
CERTIFICATE OF CORRECTION

PATENT NO.    : 6,358,720 B1
DATED         : March 19, 2002
INVENTOR(S)   : Masaaki Muramatsu et al.

It is certified that error appears in the above-identified patent and that said Letters Patent is hereby corrected as shown below:

Title page, Item [54] and Column 1, line 1,
"THEONINE" should be -- THREONINE --.

Title page,
Item [56], U.S. PATENT DOCUMENTS, insert:
--     5,863,780    Jan. 26, 1999    Au-Young et al.    435    194
       5,965,365    Oct. 12, 1999    Bandman et al.     435    6
       5,985,635    Nov. 16, 1999    Bandman et al.     435    194
       6,013,500    Jan. 11, 2000    Minden             435    194
OTHER PUBLICATIONS
Ogura et al., "Caenorhabditis elegans unc-51 gene required…," Genes & Development, Vol. 8, pp. 2389-2400, 1994
Yan et al., "Identification of Mouse ULK1, a Novel Protein…," Biochemical and Biophysical Research Communications, Vol. 246, pp. 222-227, 1998
Goshima et al., "Collapsin-induced growth cone collapse…,", Nature, Vol. 376, pp. 509-514, 1995
Serafini et al., "The Netrins Define a Family of Axon…," Cell, Vol. 78, pp. 409-424, 1994
Chan et al., "UNC-40, a C. elegans Homolog of DCC…," Cell, Vol. 87, pp. 187-195, 1996
Hanks et al., "The Protein Kinase Family: Conserved Features…," Science, Vol 241, pp. 42-52
Tomoda et al., "A Mouse Serine/Threonine Kinase Homologous…," Neuron, Vol. 24, pp. 833-846, 1999
Yan et al., "Mouse ULK2, a novel member of the UNC-51-like…," Oncogene, Vol. 18, pp. 5850-5859, 1999
Kuroyanagi et al., "Human ULK1, a Novel Serine/Threonine Kinase…," Genomics, Vol. 51, pp. 76-85, 1998
Ogura et al., "The UNC-14 protein required for axonal…," Genes & Development, Vol. 11; pp. 1801-1811, 1997
Item [57], ABSTRACT,
Line 1, "CDNA" should be -- cDNA --.

UNITED STATES PATENT AND TRADEMARK OFFICE
CERTIFICATE OF CORRECTION

PATENT NO. : 6,358,720 B1
DATED : March 19, 2002
INVENTOR(S) : Masaaki Muramatsu et al.

It is certified that error appears in the above-identified patent and that said Letters Patent is hereby corrected as shown below:

Column 7,
Line 64, "PME" should be -- pME --.

Column 8,
Line 62, "32P" should be -- $^{32}P$ --.

Column 64,
Lines 21-30, "cultural" should be -- cultured --.

Signed and Sealed this

Twelfth Day of August, 2003

JAMES E. ROGAN
*Director of the United States Patent and Trademark Office*